United States Patent
Seidler

(10) Patent No.: US 10,362,853 B2
(45) Date of Patent: Jul. 30, 2019

(54) SWIVEL LIP APPLICATOR

(71) Applicant: CONCEPT WORKSHOP WORLDWIDE, LLC, New York, NY (US)

(72) Inventor: Stewart Seidler, New York, NY (US)

(73) Assignee: CONCEPT WORKSHOP WORLDWIDE, LLC, New York, NY (US)

(*) Notice: Subject to any disclaimer, the term of this patent is extended or adjusted under 35 U.S.C. 154(b) by 0 days.

(21) Appl. No.: 15/646,354

(22) Filed: Jul. 11, 2017

(65) Prior Publication Data

US 2017/0347773 A1    Dec. 7, 2017

Related U.S. Application Data

(63) Continuation-in-part of application No. 15/056,643, filed on Feb. 29, 2016, now Pat. No. 9,700,119.

(60) Provisional application No. 62/239,613, filed on Oct. 9, 2015.

(51) Int. Cl.
| | |
|---|---|
| *B43K 5/06* | (2006.01) |
| *A45D 40/02* | (2006.01) |
| *A45D 40/22* | (2006.01) |
| *A61M 35/00* | (2006.01) |
| *A45D 40/00* | (2006.01) |

(52) U.S. Cl.
CPC ......... *A45D 40/023* (2013.01); *A45D 40/221* (2013.01); *A45D 40/222* (2013.01); *A61M 35/003* (2013.01); *A45D 2040/0025* (2013.01); *A45D 2040/225* (2013.01)

(58) Field of Classification Search
CPC .... A45D 40/22; A45D 40/221; A45D 40/222; A45D 2040/22; A45D 2040/222; A45D 2040/223; A45D 2040/224; A45D 2040/225; A45D 2040/226; A45D 2040/227; A45D 2040/228
See application file for complete search history.

(56) References Cited

U.S. PATENT DOCUMENTS

| | | | |
|---|---|---|---|
| 1,734,116 | A | 11/1929 | Coryell |
| 2,540,304 | A | 2/1951 | Thomsen |
| 2,552,903 | A | 5/1951 | Natalicchio |
| 4,915,527 | A | 4/1990 | Asano |
| 7,780,037 | B2 | 8/2010 | Corbellini |
| 9,700,119 | B1 | 7/2017 | Seidler |
| 2008/0142532 | A1 | 6/2008 | Corbellini et al. |

OTHER PUBLICATIONS

Extended European Search Report issued by the European Patent Office dated Feb. 26, 2019 in corresponding European Patent Application No. 16854427.8.

*Primary Examiner* — Jennifer C Chiang

(74) *Attorney, Agent, or Firm* — Carter, DeLuca & Farrell LLP

(57) ABSTRACT

An applicator and dispensing device adapted to enclose a solid product within a holder which is enclosed by an outer shell. The outer shell can rotate relative to the holder via a hinge and then push a support cup that contains the product along a channel and through an orifice in the holder, thus exposing the product for use. In an embodiment, the holder contains an indentation or hole that locks with a corresponding peg located the outer shell when closed. In an embodiment, the holder and outer shell are prevented from moving longitudinally relative to one another by virtue of configuring the lower position of the guideway such that it beneficially locks with the guide when the device is in a closed position.

12 Claims, 28 Drawing Sheets

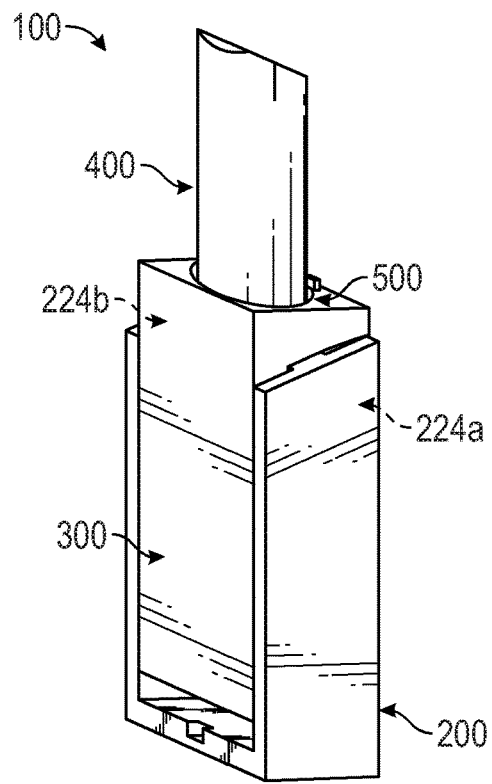
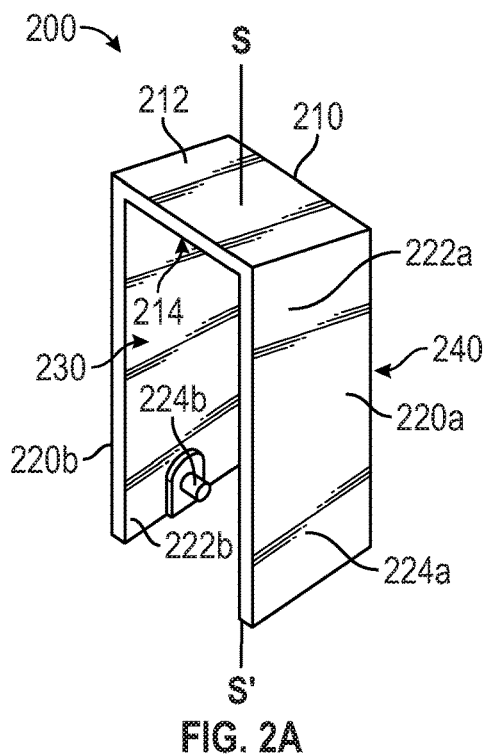
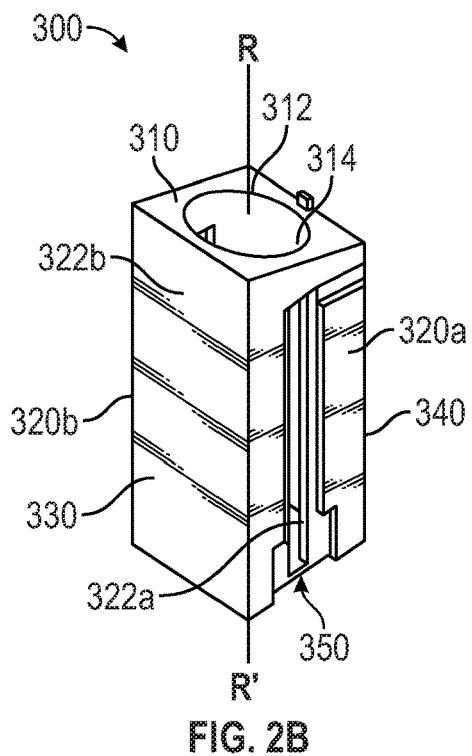
FIG. 1
FIG. 2A
FIG. 2B

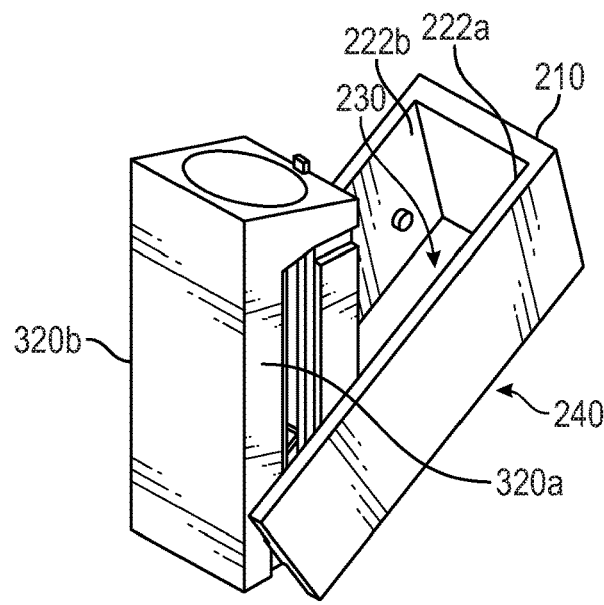
FIG. 3B
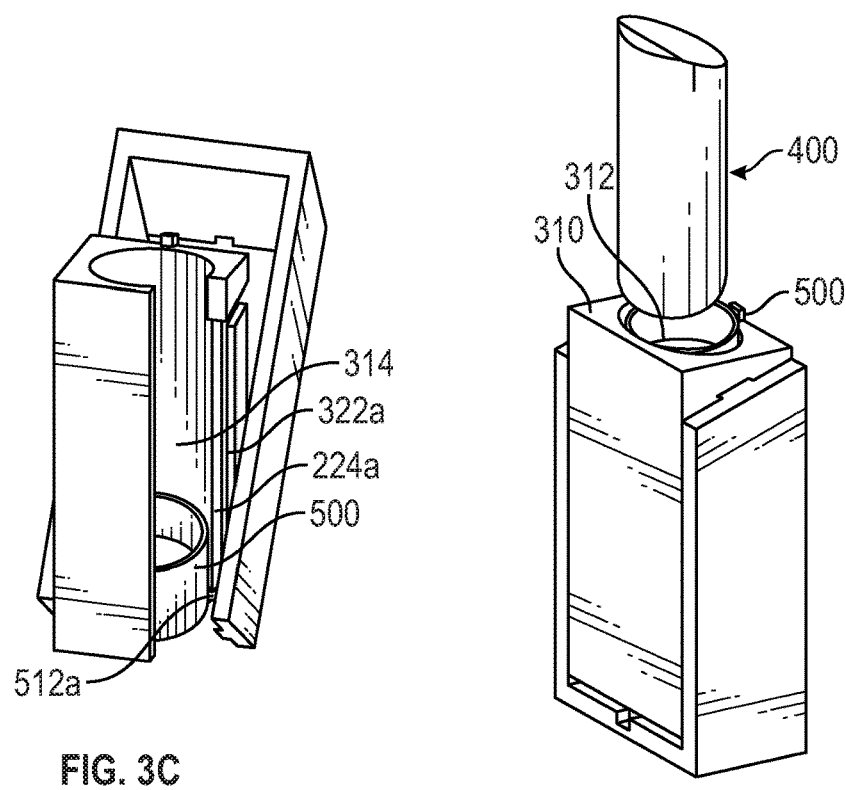
FIG. 3C
FIG. 3D

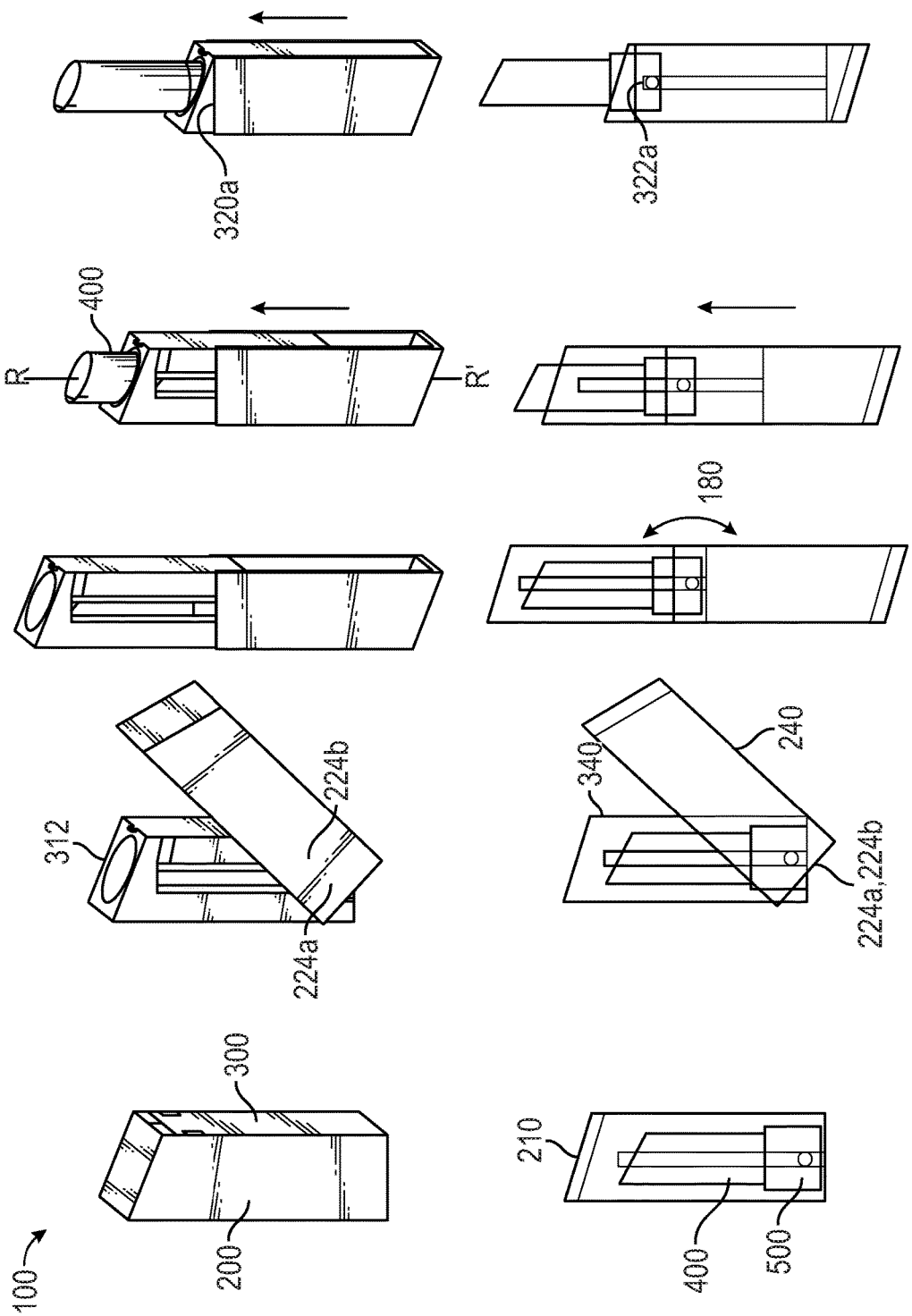

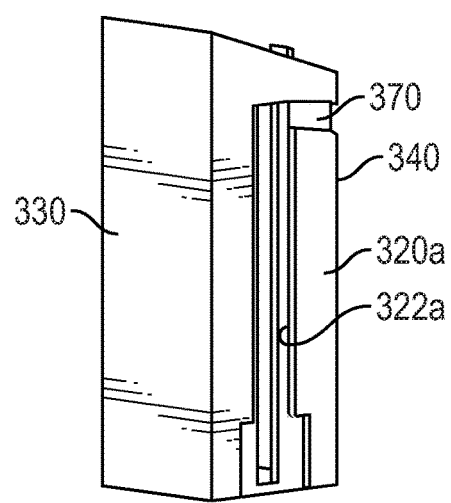
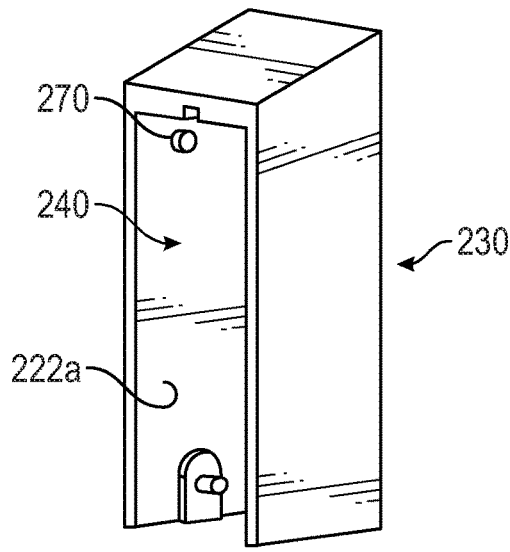
FIG. 7A  FIG. 7B
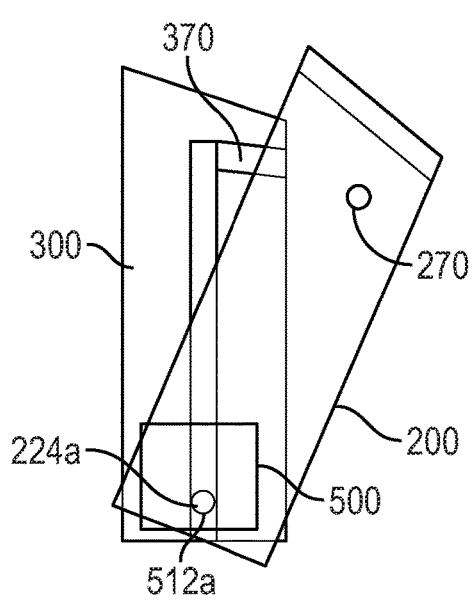
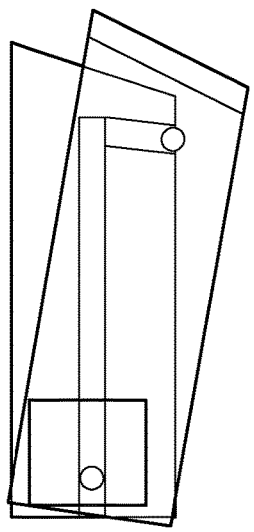
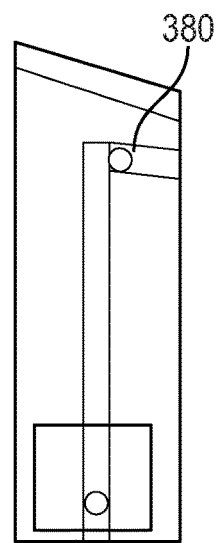
FIG. 7C  FIG. 7D  FIG. 7E

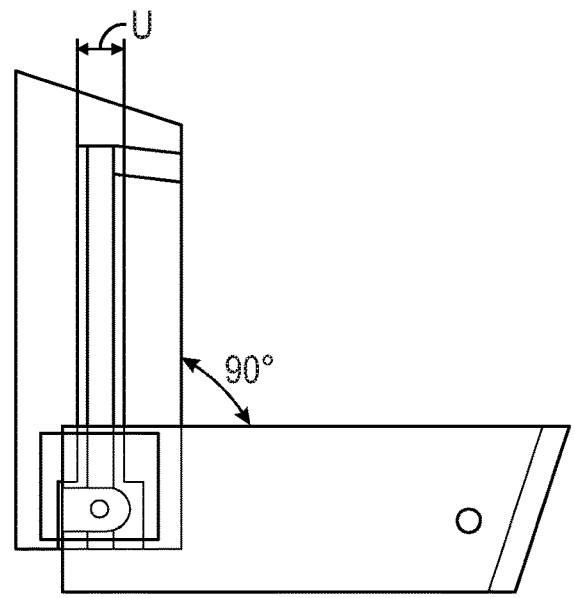
FIG. 9C
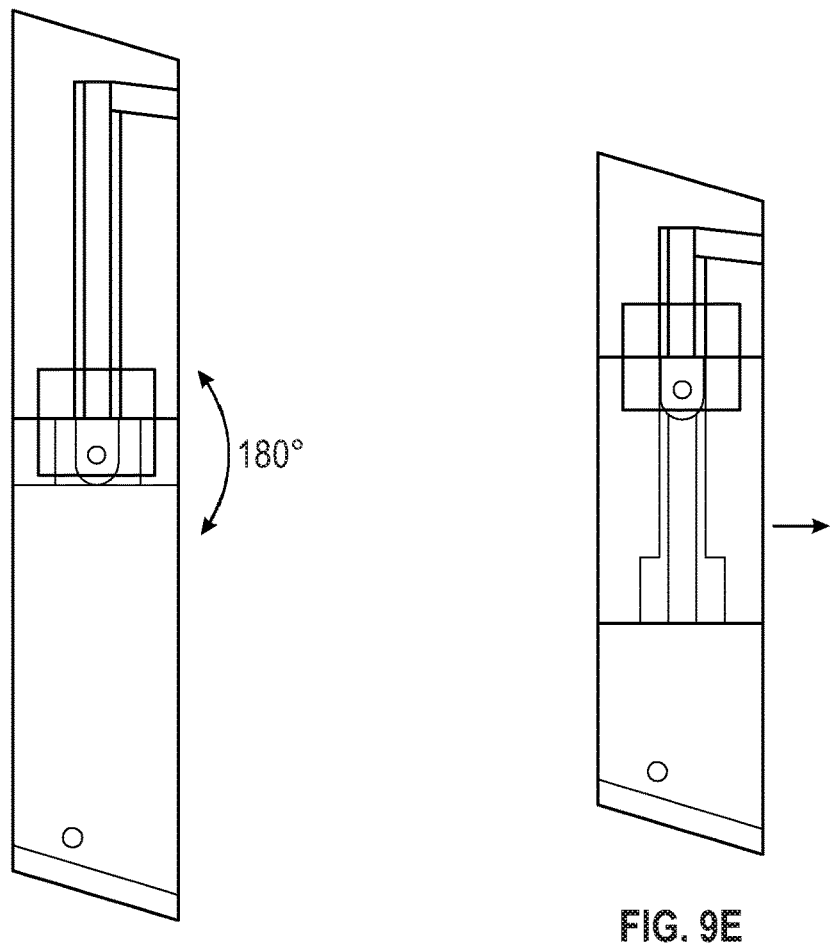
FIG. 9D
FIG. 9E

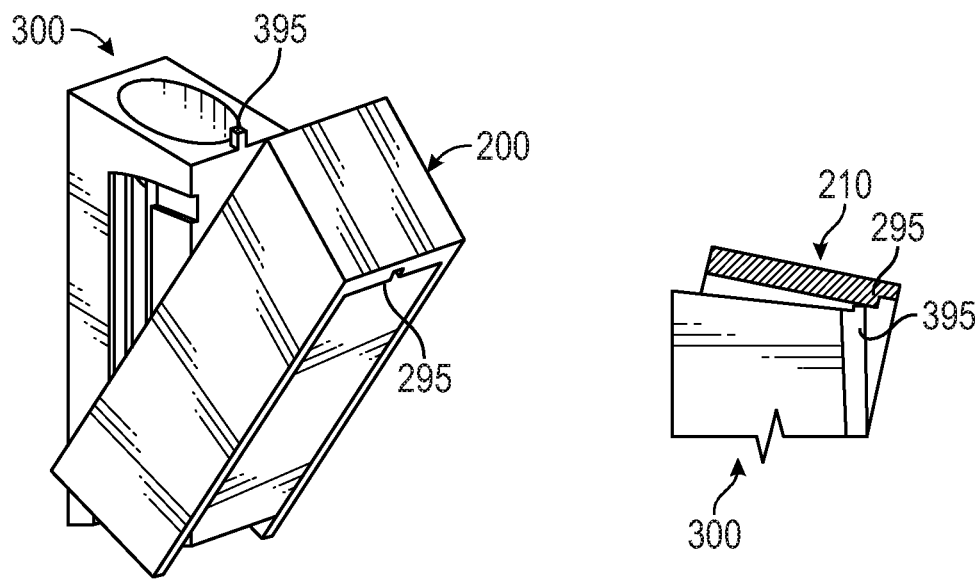
FIG. 10A
FIG. 10B
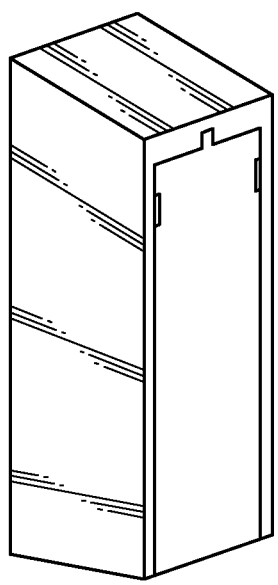
FIG. 11A
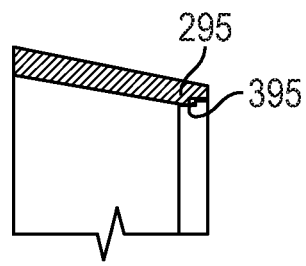
FIG. 11B

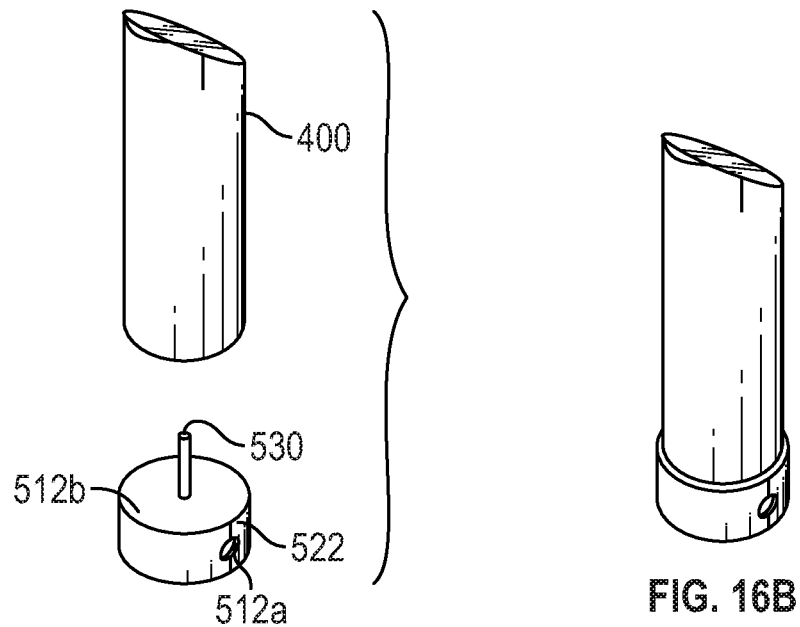
FIG. 16A
FIG. 16B
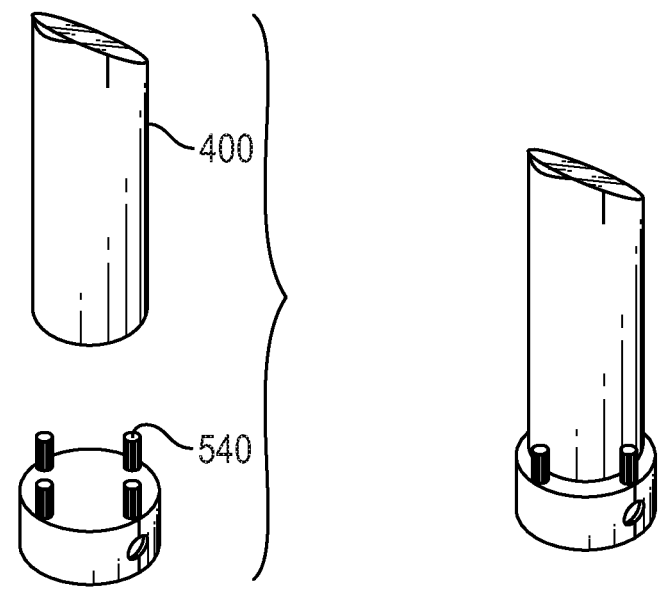
FIG. 17A
FIG. 17B

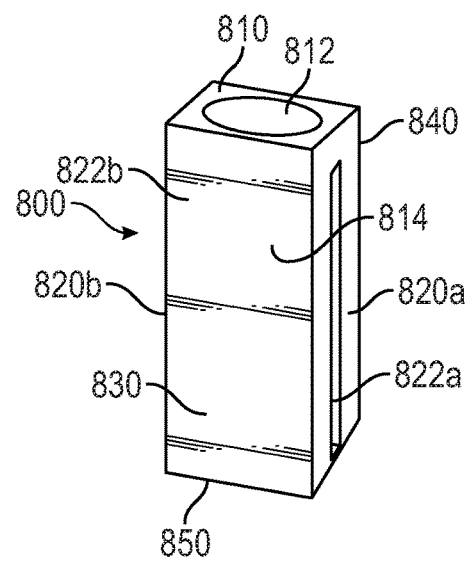
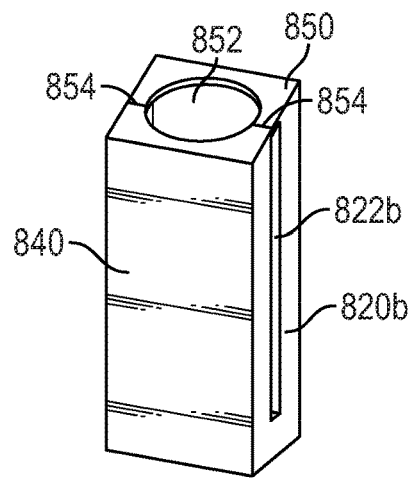
FIG. 21C
FIG. 21D
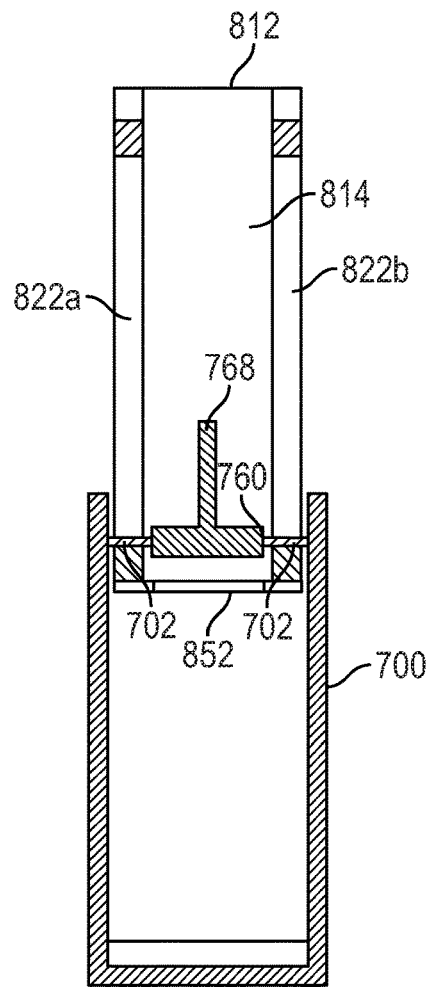
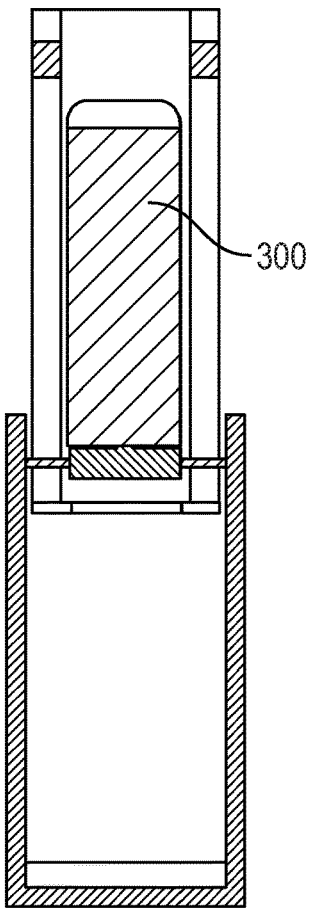
FIG. 22a
FIG. 22b

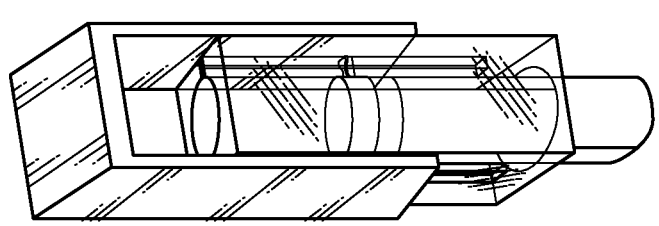 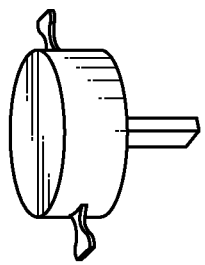
FIG. 23F
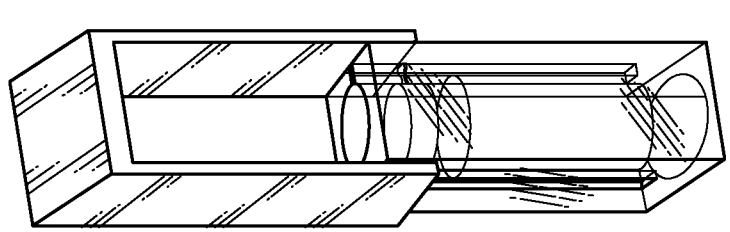 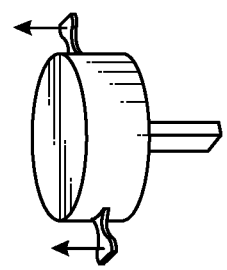
FIG. 23E
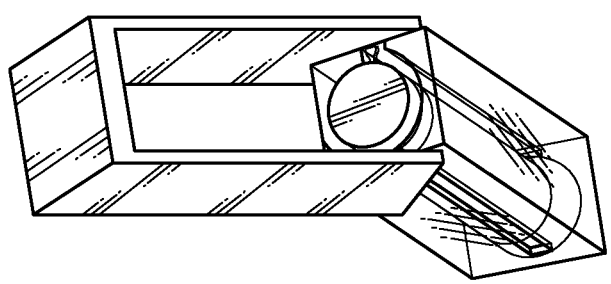 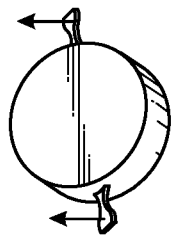
FIG. 23D

SWIVEL LIP APPLICATOR

CROSS-REFERENCE TO RELATED APPLICATIONS

This application is a continuation-in-part of PCT Application No. PCT/US2016/055995, filed Oct. 7, 2016, entitled "FLIP LIP APPLICATOR", and is a continuation-in-part of U.S. application Ser. No. 15/056,643 filed Feb. 29, 2016, entitled "FLIP LIP APPLICATOR", and claims priority to U.S. Provisional Patent Application No. 62/239,613, filed Oct. 9, 2015, entitled "SWIVEL LIP APPLICATOR." The entire contents of each of the above applications are incorporated herein by reference.

INTRODUCTION

Embodiments described herein relate generally an applicator or a dispensing device, and more particularly, to an applicator or a dispensing device for a solid or semi-solid cosmetic, medical, topical or fragrance product. Examples include, but are not limited to, a lipstick, solid ointment, eye liner, solid fragrance, topical ointment, or insect repellent.

Common packaging for solid lipsticks and similar products currently on the market can be characterized by a few design groups. For instance, one common packaging design comprises a base containing a solid lipstick embedded in a built-in cup. The base is generally covered with a tightly fit cap that is removable for application. Though this packaging type is comparatively inexpensive, removal of the cap often damages the embedded lipstick.

A similar common packaging design comprises a lipstick base, a removable cap and a set of components that rotates the base to allow the product to emerge perpendicularly to the motion of rotation. This motion usually requires a user to set the cap aside and use two hands to rotate the base in two opposite directions. This packaging design is more expensive as it typically requires four or more components for assembly.

Yet another common packaging design comprises a lipstick base, a removable cap and a set of components that allows a user to laterally slide the product through an orifice in a lipstick holder. This mechanism, however, is difficult to control and adjust the amount of product that the user wishes to expose. A variation to this slide action utilizes a rack and pinion concept. A toothed rack is attached to the internal lipstick holder and a round wheel gear extends through the outside shell. The consumer rotates the gear with the thumb and through a complimentary set of gear teeth forces the internal holder to push the product in a lateral motion. This design, while allowing the consumer to use one hand to extend and retract the lipstick, still requires the user to remove the cap, and it is frequently difficult to use the slide or rotate the wheel.

Another package represented by patent U.S. Pat. No. 7,780,037 teaches a cover that is laterally extended relative to a product-containing base. It then is rotated 180° when fully extended and again laterally adjusted to an appropriate length suitable to apply cosmetic product. In order to prevent the unit from unintentionally extending, a latch or other standard closure must be incorporated into the cover and base This action cannot be easily conducted with one hand as the consumer must forcibly pull apart the cover and base with two hands, then rotate and, then laterally compress the unit.

Furthermore, the empty package would need to be filled in an open position. Fragile product would be completely exposed as the cover rotates over it, and while the cover and base contract into a closed position. This set of actions present opportunities for damage to the product.

If the product needs to be sealed by the consumer, and the product formulation requires air or water tight closures, the consumer would need to carefully and with a steady hand, place a sealing cap about the fully extended and unprotected product so as again not to damage it.

Embodiments described herein provide an inexpensive applicator or a dispensing device that in most cases described, can be opened, adjusted and closed with one hand and without the need for removing a cap. Furthermore, embodiments described herein allow the device to be filled safely, without damaging the product or, in order to address the needs of special formulations of products, to be repeatedly sealed with a plug by the consumer without concern for inadvertently breaking the product. In one or more embodiments, a product support such as a cup containing a solid or semi-solid product is enclosed within the cavity of an elongated holder made up of at least two opposing flat sides and two opposing exposed sides. The cavity and the holder share a common longitudinal axis. The cavity is exposed to the outside through an orifice at a top end of the holder. The holder contains a pair of slots that are parallel to the holder's longitudinal axis, and that penetrates and extends along its flat sides.

One embodiment provides an applicator comprising a body having a first top surface including an opening, a channel extending through the body away from the opening of the first top surface, and a first side and a second side including a first slot and a second slot respectively cut through the first and second sides; a cover having a second top surface, a first arm and a second arm extending away from the second top surface, and a first and second hinges installed on the first and second arms respectively; and a support cup having a side wall, an inner-body opening configured to receive a product, and a first and second recesses inscribed on opposite sides of the side wall; wherein the support cup is slidably fitted inside the channel of the body and the cover is hingedly coupled to the body via the first and second hinges of the cover; and wherein the first and second hinges protrude through the first and second slots of the body and engage with the first and second recesses of the support cup, respectively, and the cover and the support cup are slidable together in a longitudinal direction along the channel of the body.

In one embodiment, there is an outer shell that comprises a cover at an upper section, from which extend two flat arms comprising a lower section. A set of rotational hinges protrudes from the inner surface of the shell arms and though the holder slots. The hinge is connected to the cup via a pair of holes or recesses within the cup. In its closed position, the two arms of the shell cover the two sides of the holder and the shell cover is positioned over the holder's orifice.

One embodiment includes a peg and groove feature that restricts the holder to a rotational motion relative to the shell when the device is closed. The exposed sides of the holder are open to the outside. When a force is applied to the front of the holder, the holder and cup restrictedly swivels in a circular motion relative to the shell, with the hinges as the centers of rotation. When the shell is thus rotated, the shell's cover exposes the holder's orifice.

In this embodiment, the holder,may be fitted with an indentation in place of a groove, such that it engages with the peg when the unit is closed, thus again restricting lateral movement. The engagement between the indentation and peg completely prevents the shell from moving laterally relative to the holder and requires a small amount of force to push out the shell relative to the holder. This design acts as a closure for controlling the rotational movement.

Another embodiment incorporates a locking mechanism between the region around the outer shell's rotational hinges such that it engages with indentations built within the lower portion of the holder such that it prevents lateral movement until after the device is rotated open.

One embodiment includes an inbuilt set of shell guides the move through dedicated guide ways built into the holder that restrict the shell from moving along the holder's longitudinal axis until the shell rotates approximately 180 degrees relative to the holder. When the shell thus rotates to 180 degrees, the user pushes the shell towards the orifice and the shell's guides can move along the holder's guide ways, and in doing so push the cup and product through the holder orifice, thus presenting the product for use.

In one embodiment, there is a mechanical or magnetic closure that secures the shell cover to the holder when the device is in a closed position and prevents it from rotating until a desire force is exerted to the front of the holder.

One embodiment prevents the holder and shell from moving relative to each other along their shared longitudinal axis while the user applies the product. In this embodiment, the arms of the shell are sufficiently flexible such that the user can squeeze the arms together so that they engage with the holder's flat sides such that the components are held in place relative to one another.

It is preferred for the holes or recesses in the cup to align with the slots in the holder during assembly so that the shell's hinge can engage with the shell's hinges. A preferred method to prevent the cup from rotating relative to the holder during assembly is to design the cup and holder cavity with non-circular cross-sectional shapes such as a square or an oval.

One embodiment is such that the shell hinge engages the cup on only one side of the applicator.

One embodiment comprises a product container platform that holds the product by a set of support columns or a stake that embeds into the product. The product may also be embedded in a foam applicator.

A preferred method to fill the applicator with product is to fully assemble the applicator and insert the product into the cup when the cup is positioned close to the orifice of the holder.

One embodiment comprises a sealing closure comprising a roof and a tube, inserted into the holder such that the tube surrounds the product, engages the outer rim of the cup, and seals the product against the outside environment.

One embodiment comprises a two-piece unit comprising an outer shell and a holder that is connected to the cup via a set of living hinges. As the shell rotates relative to the cup and holder, the hinges distort to allow the rotation.

Exemplary material for manufacturing one embodiment comprises a plastic such as ABS or PE. Parts may also be selectively constructed of a metal such as aluminum, a composite, or paper. A two-piece embodiment requires the holder and cup to consist of a flexible material such as polypropylene.

One or more embodiments provide the advantage of a device capable of dispensing a product using a low cost package while limiting exposure of the product to the environment when it is not in use.

One or more embodiments provide the advantage of a very low cost sampler dispensing device.

One or more embodiments provide the advantage of a device that presents a novel method to enclose and dispense product, which is aesthetically pleasing, and whose design offers large flat surface areas for package decoration.

One or more embodiments provide the advantage of a device that allows the user to dispense product using only one hand.

One or more embodiments provide the advantage of a container that may be filled with a product in an efficient manner.

One or more embodiments may contain a solid, semisolid, or foam embedded lipstick. The device may also contain a solid perfume, topical ointments, eye and face makeup, as well as non-cosmetic applications as topical cleaners, glues, and wax as typically used repair furniture surfaces.

One or more embodiments provide an applicator comprising a body having a first top surface including a top opening, a bottom surface including a bottom opening and a pair of slits, a channel extending from the top opening to the bottom opening, and a first side and a second side including a first slot and a second slot respectively cut through the first and second sides rising from edges defined by the first and second sides and the bottom surface; and a cover having a second top surface, a first arm and a second arm extending away from the second top surface, and a platform connected to the cover via one or more living hinges; wherein the platform is slidably inserted into the channel of the body via the bottom opening and is configured to receive a product using a stake protruding from the platform; and wherein the cover is hingedly coupled to the platform and the body via the living hinges and is slidable in a longitudinal direction along the channel via the first and second slots of the body.

BRIEF DESCRIPTION OF THE DRAWINGS

FIG. 1 is an isometric view of key components of an applicator device in its most basic form, according to an embodiment.

FIGS. 2A-2D depict isometric exploded views showing the key components of the applicator device.

FIGS. 3A-3D are isometric views showing assembly of the basic components of the applicator device.

FIGS. 4A-4E are a sequential set of isometric and corresponding cross-sectional views showing basic operation in opening the applicator device.

FIGS. 7A-7E are various views of the applicator device incorporating a peg and groove mechanism.

FIGS. 9A-9E are a sequential set of cross-sectional side views showing basic operation of the guide and guideway system as incorporated in the applicator device.

FIGS. 10A-10B show respectively isometric and partial sectional side view of the applicator device incorporating a closure mechanism in a partially open position.

FIGS. 11A-11B show respectively isometric and partial sectional side view of the same applicator device as described in FIGS. 10A-10B in a closed position.

FIG. 16A-16B show isometric views of a platform containing a product using a stake.

FIG. 17A-17B show isometric views of a platform containing a product using four support columns.

FIGS. 21A-21D show an exemplary two-piece applicator device according to an embodiment.

FIGS. 22A-22B are cross-sectional front view of the two-piece applicator device containing a product in an open position.

FIGS. 23A-23F show a sequence of isometric drawing showing complete assembly of the two-piece applicator device in various positions as it progresses from a completely closed position to an open position.

DETAILED DESCRIPTION OF SELECT EMBODIMENTS

Figure 2C:
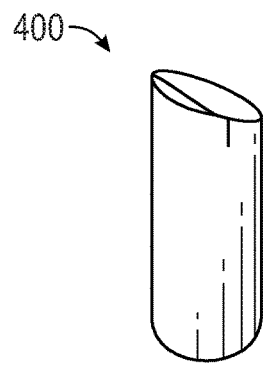

Illustrative embodiments relate to an applicator or a dispensing device adapted to enclose a solid or semi-solid cosmetic, medical, topical, or fragrance product including, but not limited to, a lipstick, solid ointment, eye liner, solid fragrance, topical ointment, or insect repellant.

Referring now to FIG. 1, an applicator device 100, according to an embodiment, comprises an outer shell 200, a holder 300, a product 400 and a support cup 500. As illustrated in FIG. 1, the outer shell 200 connects to the holder 300 via a first hinge 224a and a second hinge 224b (hidden in FIG. 1, described in more detail below) such that the outer shell 200 and the holder 300 can rotate relative to one another around an axis through the hinges.

The applicator device 100 as shown in FIG. 1 is configured to package and dispense the product 400 (e.g., a solid lipstick). The device is, of course, not restricted to this application and, in fact can be configured and dimensioned to contain any number of solid, semi-solid, or liquid products including skin care products, foam encapsulated liquids, or fragrances.

Referring now to FIGS. 2A-2D, components that are generalized in FIG. 1 are described in greater detail.

FIG. 2A shows the outer shell 200 comprising a cover 210 having a topside 212 and an underside 214. The outer shell 200 further comprises a first arm 220a and a second arm 220b extending perpendicularly from the underside 214 of the cover 210 and a front opening 230 and a back opening 240. Lengths of the first arm 220a and the second arm 220b extend sufficiently to enclose the holder 300 in a manner to be described below. The first and second arms respectively comprise a first interior 222a and a second interior 222b. These interiors may be designed with relatively flat surfaces.

FIG. 2A shows an S-S' axis that extends through the cover 210 in a direction parallel to the front and back openings and the first and second arms. At the far ends of the respective first and second interiors 222a and 222b, a first hinge 224a and second hinge 224b extends perpendicularly from the first and second interiors. The hinges are constructed at an approximate midpoint between the front opening 230 and the back opening 240. The overall configuration of the outer shell 200 as described above allows the holder 300 to rotate out of the outer shell 200 via the front opening 230 and the back opening 240, which are correspondingly dimensioned.

FIG. 2B shows the holder 300 comprising a top surface 310 with an orifice 312 that leads into a channel 314 for inserting a product. The holder 300 has a first side 320a, a second side 320b, a front side 330 and a back side 340. A first slot 322a and a second slot 322b are cut through the walls of the respective first and second sides. The length of the holder 300, the length of the channel 314 and the lengths of the first and second slots 322a and 322b, run parallel to an R-R' axis and extend approximately to a bottom surface 350.

FIG. 2C shows the product 400, in this case being a cylindrically shaped lipstick bullet with a slanted top surface designed for easy application to the lips. This product shape and form is merely an example of a standard lipstick shape found in the market place and the embodiments can package and dispense any number of product shapes and sizes and is not limited to any one shape as long as the product can be inserted and contained within the channel 314 of the holder 300.

Figure 2D:
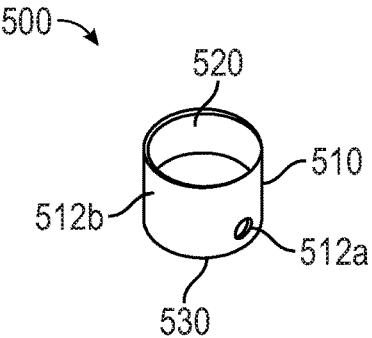

FIG. 2D shows the support cup 500 which in this case is a circular cup surrounded by a side wall 510, a top opening 520 and a bottom platform 530. A first recess 512a and a second recess 51b are inscribed into the opposing sides of the side wall 510, with respective opening shapes and dimensions such that the outer shell's first and second hinges 224a and 224b can be inserted within and rotate relative to the support cup 500. The cross-sectional shape of the support cup 500 is such that it can be linearly inserted through the orifice 312 and move along the channel 314 of the holder 300. Though the support cup 500 in FIG. 2D is presented as a circular cup, it will be shown below that there are other suitable configurations for the support cup 500.

With regard to the components as shown and described in reference to FIGS. 2A-2D, FIGS. 3A-3D illustrate how the four components of the embodiment may be fit together.

FIGS. 3A-3D also show a preferred (but not required) order in which to assemble these components.

Figure 3A:
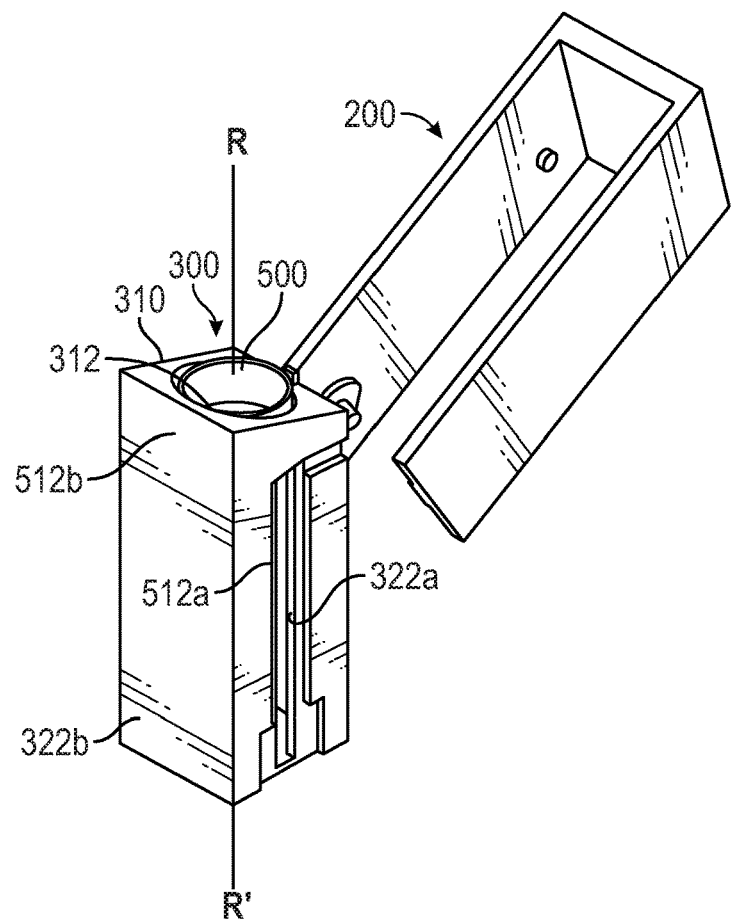

FIG. 3A shows the assembly of the support cup 500 with the holder 300. The support cup 500 is inserted into the orifice 312 and into the channel 314 with the top opening 520 of the support cup 500 facing upward such that the first recess 512a is aligned with the holder's first slot 322a and the second recess 512b (hidden from view) is also aligned with the holder's second slot 322b (also hidden from view). The first and second recesses are visible through the first and second slots, respectively, after the assembly. The support cup 500 can move freely through the channel 314 along the axis R-R'.

FIG. 3B shows how the outer shell 200 may be assembled to the holder 300 and the support cup 500. In particular, FIG. 3B shows the outer shell 200, the holder 300, and the support cup 500 at the moment of the assembly. The first and second recesses 512a and 512b, which have been aligned with the holder's first and second slots 322a and 322b, respectively, are also aligned with the first and second hinges 224a and 224b of the outer shell 200. Though it is not show in this figure, it should be assumed that the cup second recess 420b is aligned with the holder second slot 214b of the holder. Furthermore, the present embodiment reveals a holder top surface 210 and a shell cover 110 that are designed to be angled to secure the device when it is in a closed position. This detail will be explained further in FIGS. 6A-6D. As shown with FIG. 3B, the width of the holder 300 as defined by the perpendicular distance between the holder's first side 320a and the holder's second side 320b is equal to or slightly less than the perpendicular distance between the first interior 222a and the second interior 222b of the respective first and second arms of the outer shell 200. Moreover, the lengths of the first and second arms 220a and 220b of the outer shell 200 are such that they substantially cover the height of the holder's first and second sides. Lastly, the outer shell's front opening 230 and the back opening 240 are such that the holder 300 can be easily positioned between the outer shell's first and second arms.

In order to allow insertion of the outer shell's first and second hinges through the holder's slots such that they may engage with the support cup's recesses, the outer shell's arms may need to be flexed outwards to accommodate the protrusion lengths of the hinges and then return to their original shape. Thus, the outer shell's first and second arms may be composed of a suitably flexible material to allow such flexing but with a material memory such that the flexing will not permanently distort the shape of the outer shell.

FIG. 3C illustrates a cutaway view shown at an oblique angle to the other three views. FIG. 3C illustrates in detail how the first hinge 224a is inserted through the first slot 322a and engages with the first recess 512a. Though hidden from FIG. 3C, the second hinge 224b is similarly and simultaneously inserted through the second slot 322b and engages with the second recess 512b.

An exemplary design of the first and second hinges 224a and 224b is a cylindrical shape whose length is defined as the amount of protrusion from the first and second interiors of the respective arms and whose diameter is defined such that the hinges can easily fit through the holder's slots and engage with the support cup's recesses. The corresponding support cup's recesses may likewise have cylindrical shape and have diameters that are approximately equal to those of the hinges. Furthermore, the length of the hinges are such that they can fully engage the support cup's recesses having protruded through the respective thicknesses of the holder's first and second sides. This design allows any force applied to the outer shell's hinges to directly translate into a corresponding movement of the support cup along the holder's channel 314 in a manner that will be detailed later.

FIG. 3D shows the outer shell's hinges having fully engaged with the support cup's recesses. Once fully engaged, the support cup is positioned proximal to the top surface 310 of the holder 300 such that the support cup 500 is accessible through the holder's orifice 312. The product 400 is shown being inserted into the support cup 500.

The sequence for assembly of these foregoing components within the scope of the embodiments is not limited to that shown with respect to FIGS. 3A-3D. For example, the product 400 and the support cup 500 may be preassembled before the support cup 500 is inserted into the holder 300 or the outer shell 200 may first be assembled to the holder 300 before inserting the support cup 500 into the holder 300.

Referring now to FIGS. 4A-4E, a preferred sequence employed in opening the applicator device 100 and accessing the product 400 is illustrated. Each of the FIGS. 4A-4E shows an isometric illustration of a sequential segment and a corresponding two-dimensional side view of the same sequential segment.

FIG. 4A shows a closed position of the applicator device 100. The upper isometric illustration shows how the outer shell 200 completely covers and protects the product 400 within the holder 300. The lower two-dimensional side view shows the applicator device 100 in the same closed position and how the product 400 is positioned in the support cup 500. For sake of clarity, the product 400 and the support cup 500 are depicted in dashed lines.

FIG. 4B shows the outer shell 200 rotating relative to the holder 300 about the axis defined by the first hinge 224a and second hinge 224b and the orifice 312 of the holder 300 is exposed. The direction of rotation is such that the outer shell's back opening 240 moves away from the back side 340 of the holder 300. It will be shown below in detail with respect to FIGS. 6A-6D how the outer shell 200 is prevented from rotating in a direction such that the outer shell's back opening 240 and holder's back side 340 approach each other.

FIG. 4C shows the applicator device 100 after the outer shell 200 and the holder 300 have rotated 180 degrees relative to each other, from their original positions. The holder 300 is now ready to be moved longitudinally relative to the outer shell 200 along the R-R' axis. As was shown in FIGS. 3C describing the assembly of the applicator device, the outer shell's hinges 224a and 224b protrude through the holder's first slot 322a and second slot 322b and are engaged with the first and second recesses of the support cup 500. Thereafter, the product is ready to be propelled by the support cup 500 and the outer shell 200 through the holder's channel 314 and along the holder's first and second slots and in a direction parallel to the R-R' axis.

FIG. 4D shows the applicator device 100 after the outer shell 200 and the support cup 500 have begun to move simultaneously along the channel 314 in the direction indicated by the arrow.

Finally, FIG. 4E shows the applicator device 100 in a fully open position. The product 400 is fully exposed and ready to be applied. It should be understood that a normal use of the product 400 does not require it to be completely open; rather, a user may be able to access and use the product 400 even if it is only partially exposed.

Referring now to FIGS. 5A-5E, a preferred sequence employed in closing the applicator device 100 is illustrated. The sequence illustrated in FIGS. 5A-5E shows the same components and parts as illustrated in FIGS. 4A-4E but in a sequentially reversed order.

Figure 5E:
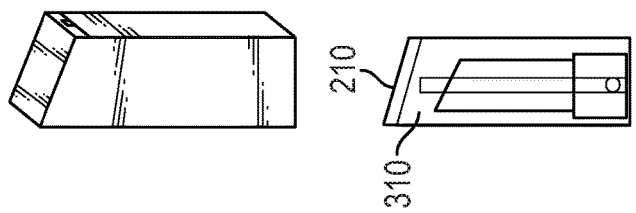
FIGS. 5A-5E are a sequential set of isometric and corresponding cross-sectional views showing basic operation in closing of the applicator device.
Figure 5D:
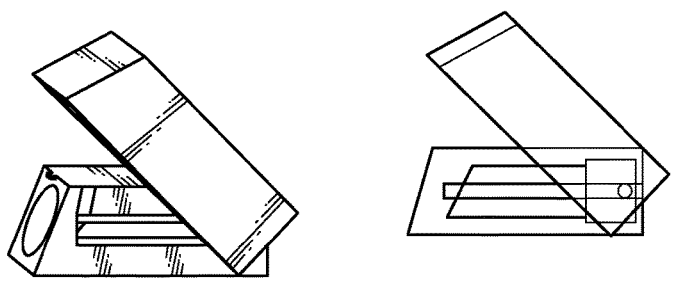
Figure 5C:
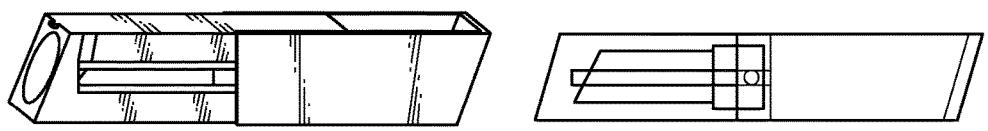
Figure 5B:
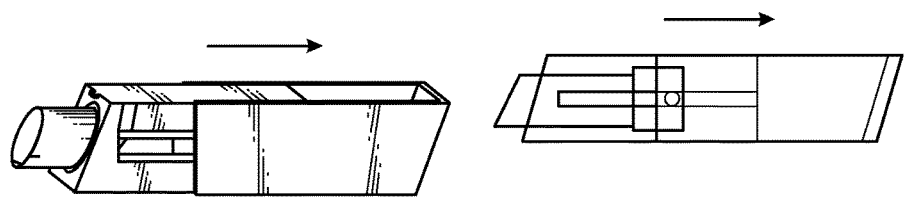
Figure 5A:
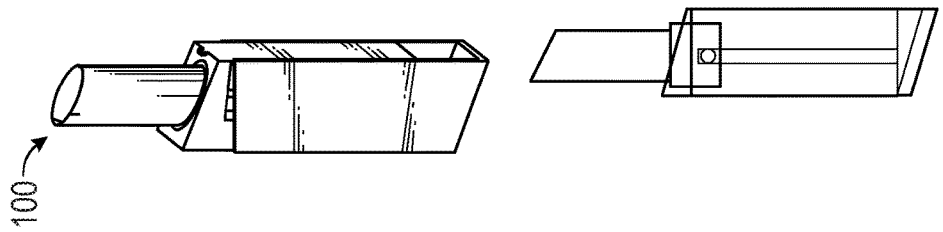

FIG. 5A shows the applicator device 100 in a fully open position. FIGS. 5B and 5C show the outer shell 200, whose hinges are engaged with the support cup's recesses, pulling the product-filled support cup away from the orifice 312 and into the channel 314 in the direction indicated by the arrow. FIG. 5D shows the outer shell 200 rotating relative to the holder 300 and product-filled support cup toward a closed position. Finally, FIG. 5E shows the applicator device 100 in a closed position, identical to what is shown in FIG. 4A. The outer shell 200 is prevented from rotating further by virtue of the angular designs of the holder's top surface 310 and the outer shell's cover 210 as will be detailed in reference to FIGS. 6A-6D.

Referring now to FIGS. 6A-6D, a set of side cross-sectional views that emphasizes the angular orientations of the top portions of the outer shell 200 and the holder 300 is illustrated.

Figure 6A:
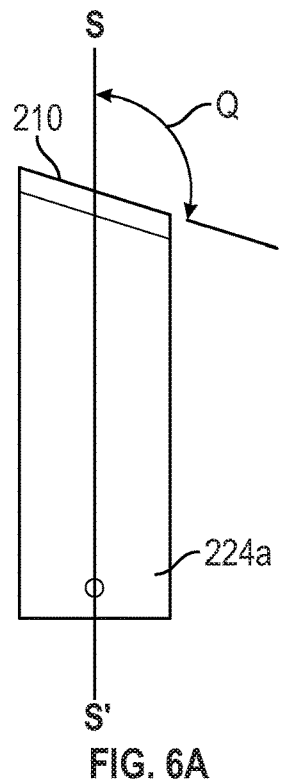
FIGS. 6A-6D are cross-sectional views detailing the angular features of the outer shell's cover and the holder's top surface when closing the applicator device.
Figure 6B:
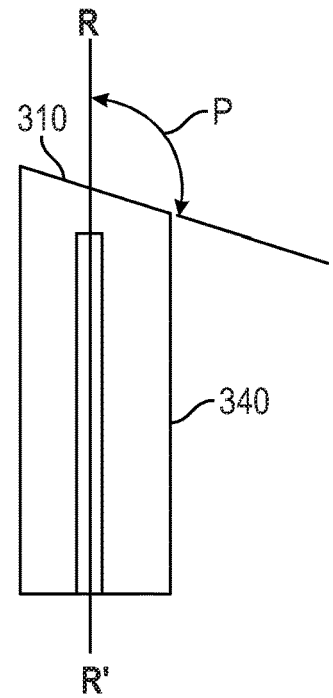
Figure 6C:
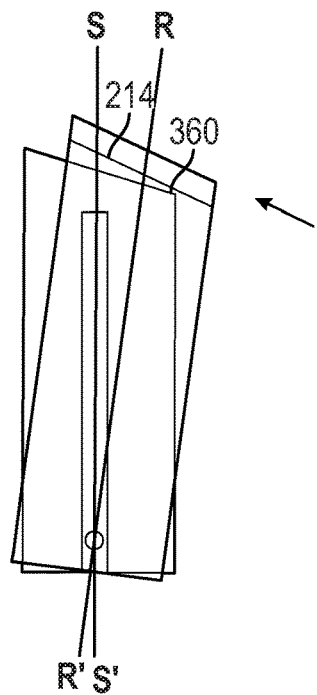
Figure 6D:
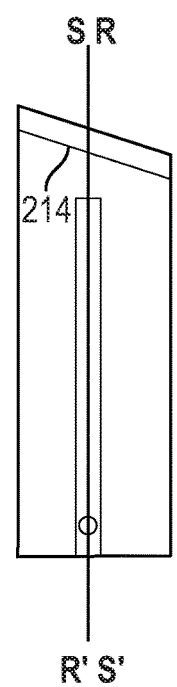

FIG. 6A shows the angular offset Q of the outer shell's cover 210 relative to the outer shell's longitudinal axis S-S'. FIG. 6B shows the angular offset P of the holder's top surface 310 relative to the holder's longitudinal axis R-R'. FIG. 6C shows the applicator device 100 as the outer shell 200 rotates about the outer shell's hinges 224a and 224b and as the outer shell cover's underside 214 is about to fully close over the holder's top surface 310. The angular offsets Q and P should be dimensioned such that when the outer shell 200 is almost closed as illustrated in FIG. 6C, an edge 360 defined between the top surface 310 and the back side 340 of the holder 300 does not interfere with the outer shell cover's underside 214. The outer shell's back opening 240 rotates into the holder's back side 340 until the outer shell 200 is forced to make a full stop as the outer shell cover's underside 214 comes in contact with the holder's top surface 310. It is the contact between these two surfaces that prevents the outer shell 200 from rotating further. The axes R-R' and S-S' incidentally approximately coincide when the applicator device 100 is in this position.

Referring now to FIGS. 7A-7C, a set of views of the applicator device 100 incorporating a peg and groove mechanism that prevents the holder from moving laterally relative to the outer shell when the applicator device is in a closed position, is illustrated.

FIG. 7A shows an isometric drawing of the holder 300 oriented such that the front side 330 can be viewed. FIG. 7A further shows a groove 370 of a given depth inscribed in the form of a circular arc, into the holder's first side 320a. An end of the arc starts from the holder's back side 340 and extends toward and eventually terminates at the first slot 322a.

FIG. 7B shows an isometric drawing of the outer shell 200 oriented such that the back opening 240 can be viewed. The outer shell comprises a peg 270 of a given height protruding from the first interior 222a of the outer shell's first arm 220a. In this illustration, the peg 270 is depicted as having a cylindrical shape. The height of the peg 270 is such that it engages with the holder's groove 370 and moves through the groove 370 unobstructed. The peg 270 may be formed into other general shapes as long as it can engage with and move through the groove 370 unobstructed. This groove and peg mechanism is constructed at a location such that when the outer shell 200 is rotated toward the holder 300 as the applicator device 100 approaches a closed position, the peg 270 will engage with the groove 370 at the holder's back side 340.

The groove's arc is such that its radial center coincides with the center of rotation of the outer shell 200 relative to the holder 300. Though this embodiment assumes the holder 300 comprising a groove and the outer shell 200 comprising a peg, in an alternative embodiment, the peg can be located on the holder's first side and the groove inscribed into the outer shell's first arm's first interior.

Even further, although only one set of peg and groove mechanism is described heretofore, a second or even multiple sets of the peg and groove mechanism may be incorporated into an applicator in order to further secure the holder to the outer shell. For instance, a peg can be located on both the first interior and second interior of the outer shell and a groove can be located on both the first side and second side of the holder.

FIGS. 7C-7E illustrates cross-sectional views of a set of three sequential segments describing how in closing the applicator device 100, the peg 270 engages with the groove 370 and secures the applicator device 100 in its closed position. The three sequence segments each shows the holder 300, the outer shell 200 and a dashed outline of the support cup 500 within the holder 300.

First, 7C shows the outer shell 200 closing against the holder 300. The first hinge 224a is engaged with the support cup's first recess 512a and the support cup is at the bottom of the holder's channel 314. The peg 270 has not yet reached the location where it contacts the groove 370. The outer shell 200 is rotating about the center of rotation as defined by the outer shell's hinges 224a and 224b.

Second, 7D shows the same rotating outer shell 200 as it moves closer to the holder 300. Here, the peg 270 has entered the groove 370. The radial dimension of the groove 370 is approximately the same as the radial movement that the peg 270 travels relative to the center of rotation.

Lastly, 7E shows the applicator device 100 in a closed position. The peg 270 has moved along the groove 370 and arrived at a contact point 380. At this point, the peg 270 prevents the outer shell 200 from moving longitudinally upwards relative to the holder 300. The angular design as described in 6a-6d prevents the shell from rotating further toward the holder front. Therefore, the shell is locked in place and is restricted to movement in the direction toward its back opening.

Referring now to FIGS. 8A-9E, a further embodiment incorporating a guide and guideway that prevents the outer shell from moving longitudinally relative to the holder is illustrated. The guide and guideway system prevents the holder 300 from rotating relative to the outer shell 200 after the hinges move longitudinally along the first and second slots 322a and 332b. In this embodiment, the applicator device 100 is more stable when opening and using the applicator device 100.

Figure 8A:
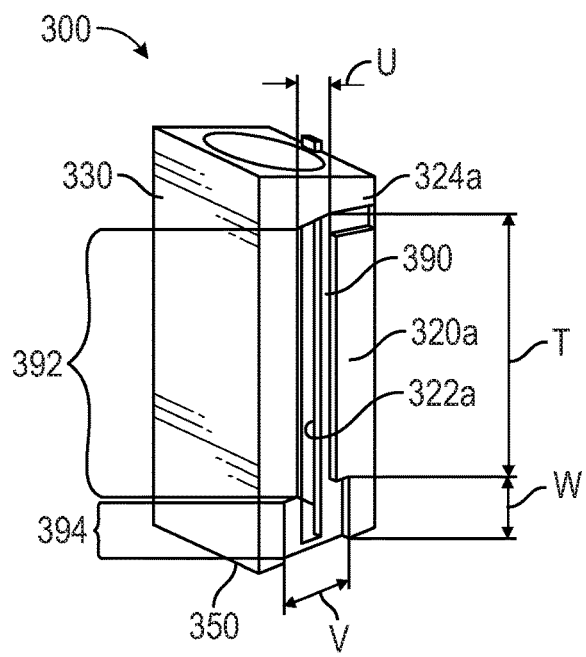
FIGS. 8A-8B are isometric views showing the applicator device incorporating a guide and guideway system.

FIG. 8A shows an isometric drawing of the holder 300 oriented such that the front side 330 can be viewed. The holder's first side 320a is inscribed with a guideway 390 that runs parallel to and borders either side of the first slot 322a. The longitudinal length of the guideway 390 approximately extends from the holder's bottom surface 350 to a first slot top 324a. The depth of the guideway does not exceed the thickness of the wall forming the holder's first side 320a. The guideway 390 is divided into an upper portion and a lower portion. The upper portion 392 of the guideway 390 is of a width U and length T. The lower portion 394 of the guideway 390 is proximal to the holder's bottom surface 350 and has a width V and length W. The width V is greater than the width U.

Figure 8B:
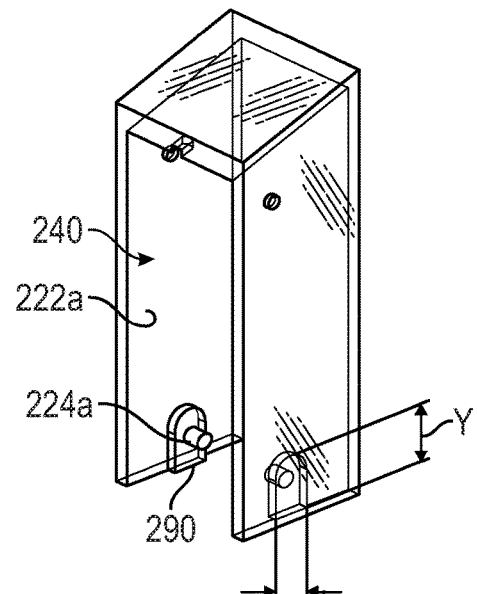

FIG. 8B shows an isometric drawing of the outer shell 200 oriented such that the back opening 240 can be viewed. From the outer shell's first interior 222a protrudes a guide 290 surrounding the first hinge 224a having a width X and length Y. The protruding height of the guide 290 is less than that of the hinge 224a but sufficient such that when the outer shell 200 and the holder 300 are assembled, the guide 290 can engage with the upper portion and lower portion of the guideway 390.

As will be detailed in reference to FIGS. 9A-9E, the guide 290 is dimensioned such that it can rotate around the axis of the hinges while the support cup 500 is proximal to the holder's bottom surface 350 and within the lower portion area defined by width V and length W. The length Y of the guide is dimensioned to be greater than the width U of the upper portion. The width X of the guide is dimensioned to be less than or equal to the width U of the upper portion. Therefore, the guide 290 limits rotation of the outer shell 200 relative to the holder 300 when the guide 290 is located within the lower portion 394. It further limits the guide 290's longitudinal movement when the guide 290 is located in the upper portion 392.

FIGS. 9A-9E illustrate the interaction between the guide 290 and the guideway 390. In FIGS. 9A-9E, the outer shell 200 is depicted as transparent in order to clearly show the interaction of the guide 290 within the guideway 390. In these drawings, the bold solid lines depict the position of the outer shell's outer boundaries and the outer shell's cover 210, the position of the guide 290 and the position of the first hinge 224a. The thin solid lines depict the holder's outer boundaries, the first slot 322a, and the guideway 390. The dashed line shows the position of the outer borders of the support cup 500.

Figure 9A:
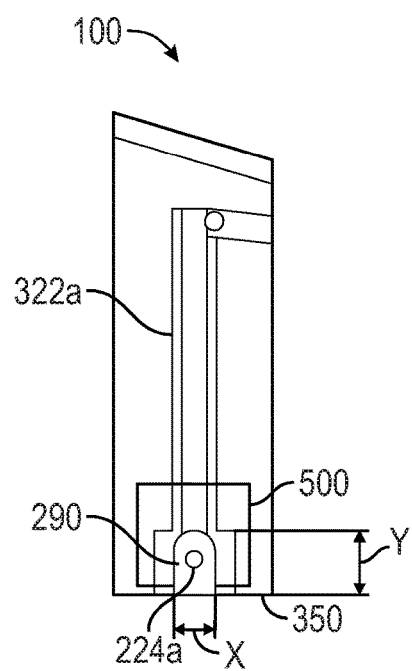

In FIG. 9A, the applicator device 100 is in a fully closed position. The support cup 500 is proximal to the holder's bottom surface 350 and connected to the outer shell 200 via the hinges 224a and 224b as described hitherto. The guide 290 is completely contained within the volume of the lower portion and has a width X and length Y. As was described above in reference to FIGS. 7A-7C, incorporation of the peg 270 and the groove 370 prevents the outer shell 200 from moving in a longitudinal direction relative to the holder 300 while in the closed position.

Figure 9B:
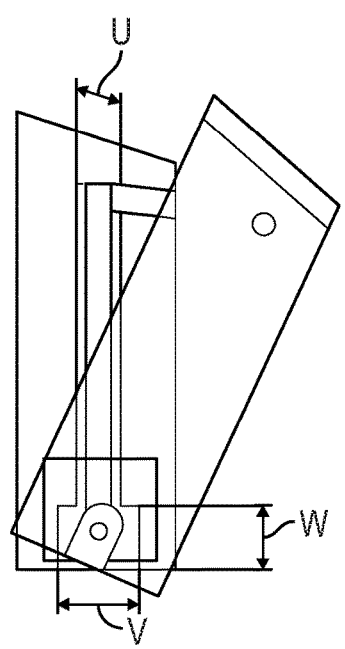

FIG. 9B shows the outer shell 200 rotating away from the holder 300. As mentioned previously, the lower portion 394 of the guideway 390 as defined by the width V and length W, allows the guide 290 to rotate within its confined space. The outer shell's peg 270 is completely disengaged from the holder's groove 370.

FIG. 9C shows the outer shell 200 after it has rotated approximately 90 degrees relative to the holder 300. Because the length Y of the guide 290 is greater than the width U of the upper portion 392 of the guideway 390, it cannot move longitudinally along the guideway's upper portion 392.

FIG. 9D shows the outer shell 200 having rotated 180 degrees relative the holder 300. Now, since the width X is less than the width U, the guide 290 is able to fit into the guideway 390 and able to propel the support cup 500 through the holder's channel 314. FIG. 9E shows the position of the support cup 500 after it has propelled some distance upward through the holder's channel 314.

Though the foregoing description of this feature is illustrated with only one guideway 390 proximal to the holder's first slot 322a and a guide 290 proximal to the first hinge 224a, the applicator device 100 can be alternatively designed such that there is a second guideway and a second guide proximal respectively to the holder second slot 322b and to the second hinge 224b. Such an addition would further stabilize the applicator device 100 during use.

FIGS. 10A-11B show yet another embodiment comprising a closure that further stabilizes the applicator device 100 when it is in a closed position. Though there are different designs of closures that may be employed, what is shown in reference to FIGS. 10A-11B is a simple mechanical snap mechanism.

FIG. 10A shows an isometric view of a closure female section 295 positioned in the underside 214 of the outer shell 200 proximal to the back opening 240. FIG. 10A also shows a closure male section 395 on the top surface 310 of the holder 300 proximal to the back side 340. In FIG. 10A, the outer shell 200 is rotating relative to the holder 300 towards a closed position. FIG. 10B shows a partial cross-sectional detailed view of the relevant area demonstrating the closure female section 295 about to engage with the closure male section 395. FIG. 11A shows the applicator device 100 in a fully closed position with the closure sections completely engaged. FIG. 11B shows a partial cross-sectional detailed view of the relevant area demonstrating the engaged closure sections.

Referring now to FIGS. 12A-12D, a set of cross-sectional views further describes the applicator device 100 when pressure is exerted on either side of outer shell's first and second arms.

Figure 12D:
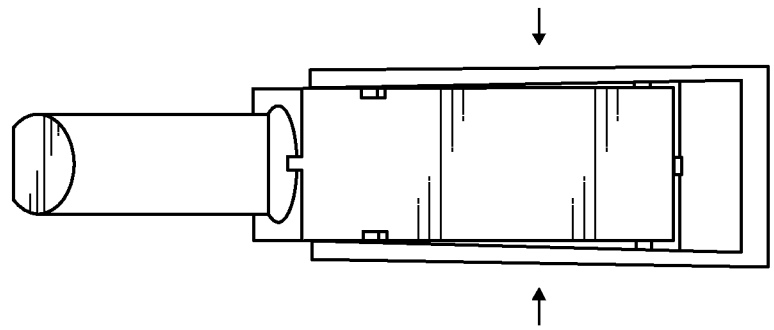
FIGS. 12A-12D show a set of front views illustrating how pressure exerted on the sides of the outer shell supports the holder during use.
Figure 12C:
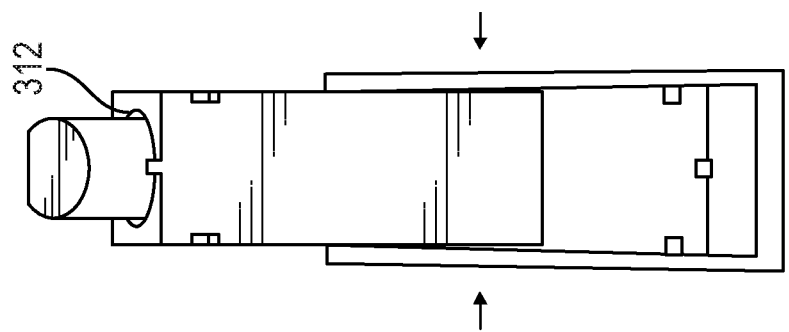
Figure 12B:
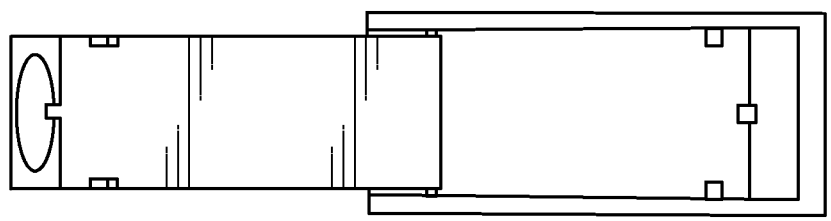
Figure 12A:
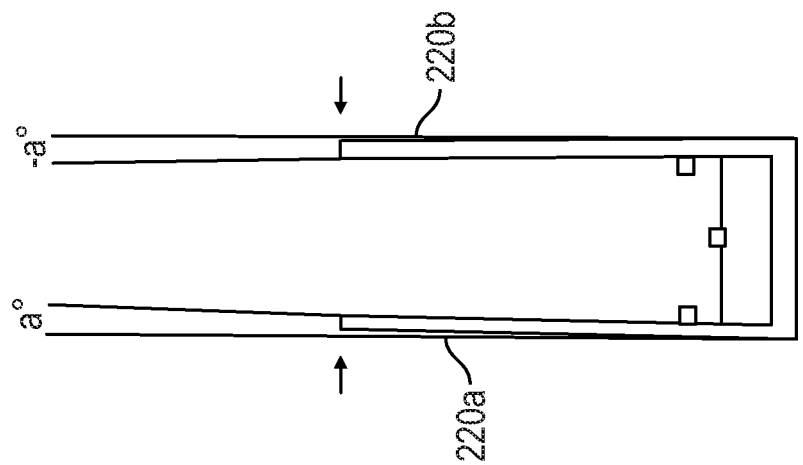

FIG. 12A is a front view of the outer shell 200 demonstrating the bending angles of the first arm 220a and the second arm 220b when pressure is exerted in directions symbolized by the shown pair of arrows. The angles a° and −a° represent the respective angle by which the first and second arms distort upon compressive force.

FIG. 12B shows the fully assembled applicator device 100 where the outer shell 200 has rotated 180 degrees with respect to the holder 300. The view in FIG. 12B is directed toward the front of the outer shell 200 and the holder 300 has not yet propelled the product 400 forward.

FIG. 12C shows the outer shell 200 having pushed the product partially through the orifice 312 of the holder 300. Pressure is exerted in the directions demonstrated by the arrows which in turn causes the arms' interiors to compress against the first and second sides of the holder 300. These compressive forces, as shown by the arrows in FIGS. 12C and 12D would usually be exerted by the user's fingers as the product is applied and by virtue of friction between the outer shell's arms against the holder's first and second sides, prevent the holder 300 from sliding longitudinally relative to the outer shell 200.

FIGS. 13A-13D demonstrate the same feature as illustrated in FIGS. 12A-12D, except that a set of notches 296 are built into one or both sides of the outer shell's arms and a set of protrusions 396 are built into the first and second sides of the holder 300 to assist the relevant compressive forces in stabilizing the applicator 100. It is to be noted that there are various designs for notches and protrusion mechanism that can be employed to achieve this result.

Figure 13D:
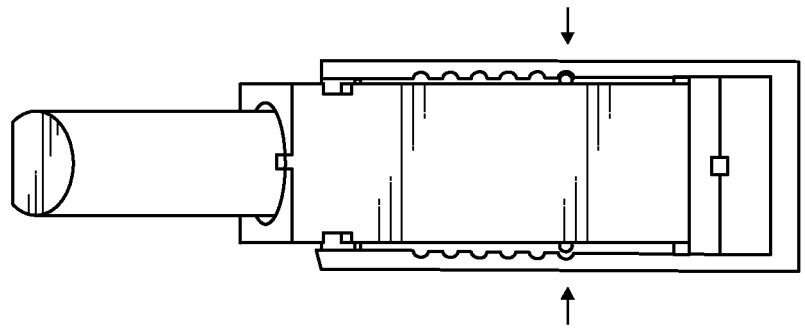
FIGS. 13A-13D show a set of isometric and front views of the applicator device incorporating a set of notches and protrusions to accentuate the grip between the outer shell and the holder when pressure is applied to the outer shell's sides.
Figure 13C:
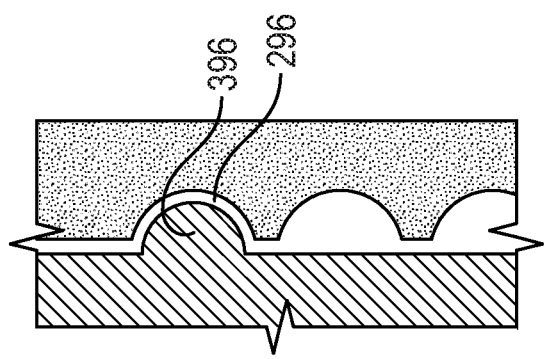
Figure 13B:
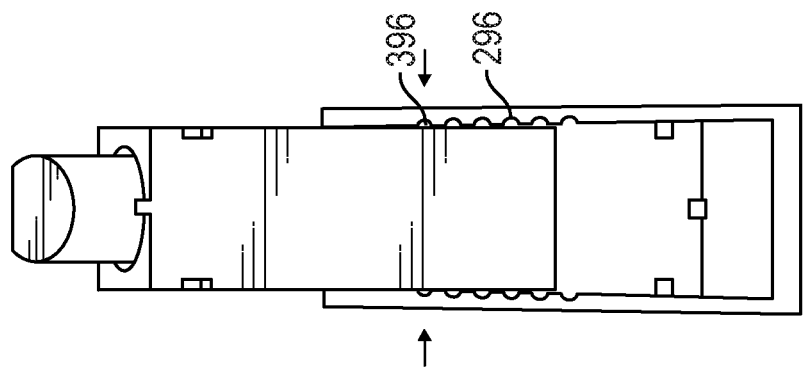
Figure 13A:
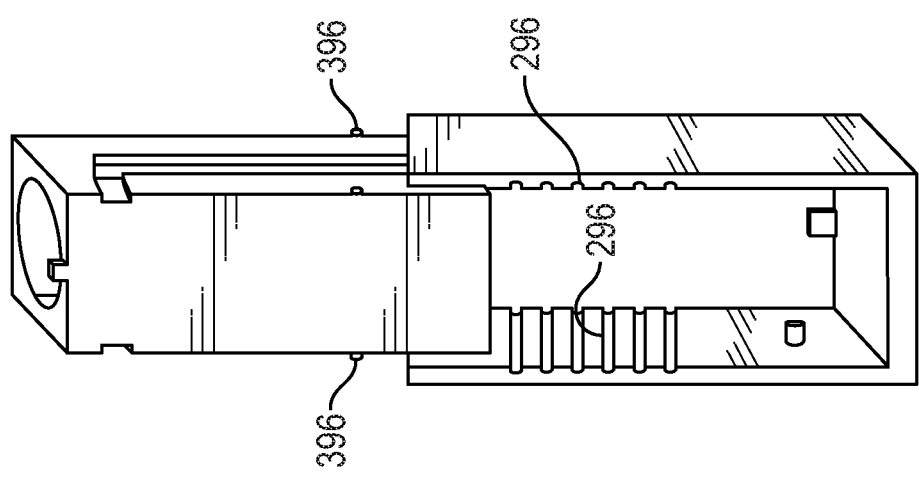

Illustrated in FIG. 13A is an isometric view of the applicator device 100 with a set of notches 296 on either side of the first and second interiors and a set of protrusions 396 extending from the holder's first and second sides.

The applicator device 100 as shown in FIG. 13B corresponds to what is shown in FIG. 12C but the holder's built-in protrusions 396 have engaged with the notches 296 built on the arms of the outer shell 200. As pressure is applied in the direction of the arrows, the arms compress against the holder and stabilize the applicator device 100. It is also shown in FIG. 13B that the holder's protrusions 396 can engage with the notches 296 at various locations longitudinally along the arms' interiors. Therefore, the holder's longitudinal position can be adjusted relative to the outer shell 200.

FIG. 13C shows a partial cutaway and magnified detail of the area comprising the engagement of the notch and the protrusion.

FIG. 13D corresponds to FIG. 12B but with the holder 300 having protrusions 396 and the outer shell having notches 296. The arrow indicates the position where the notches engage with the protrusions as compressive pressure is applied.

It is apparent from descriptions as shown in FIGS. 13A-13D that the addition of this feature accentuates the efficacy of the compressive forces between the arms of the outer shell 200 and the holder 300. Though this embodiment shows the notches built within the arms' interiors and the protrusions built on the holder's first and second side, it is obvious that the protrusions can be built on the arms' interiors and the notches built along the holder's sides. Furthermore, circular indentations can be substituted for notches; this latter design option as well as other configurations could be preferred to improve the overall aesthetic appeal of the applicator device.

Figure 14A:
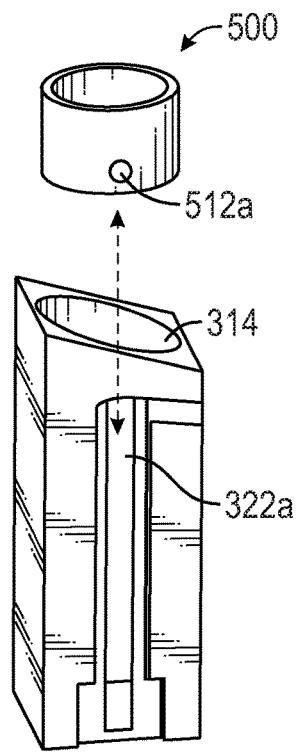
FIGS. 14A-14B show isometric views of the holder and the support cup of the applicator device having an oval shaped support cup and corresponding oval shaped orifice and channel.
Figure 14B:
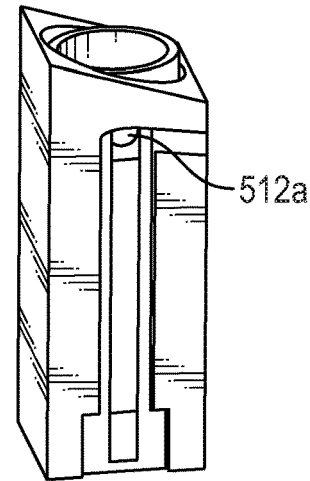

FIGS. 14A-14B show isometric views showing assembly of the holder 300 and the support cup 500 components of the applicator device 100. When the support cup 500 is circularly shaped, the support cup can rotate freely within the channel 314 of the holder 300 and make it difficult to align the support cup's first and second recesses with the holder's first and second slots. Accordingly, an oval shaped support cup and a corresponding oval orifice on the holder can provide an improved structure. In particular, any non-circularly shaped support cup can be designed such that the support cup's recesses naturally align with the corresponding slots during assembly.

FIG. 14A shows a support cup 500 whose profile is oval shaped. The holder's corresponding orifice 312 is similarly oval shaped such that the support cup 500 can fit through the orifice and move through the holder's channel without rotation. The support cup's first recess 512a is conveniently aligned to the holder's first slot 322a. FIG. 14B shows the oval shaped support cup 500 inserted within the holder 300 and the first recess 512a visible through the first slot 322a such that the first hinge 224a can engage with it.

Figure 15A:
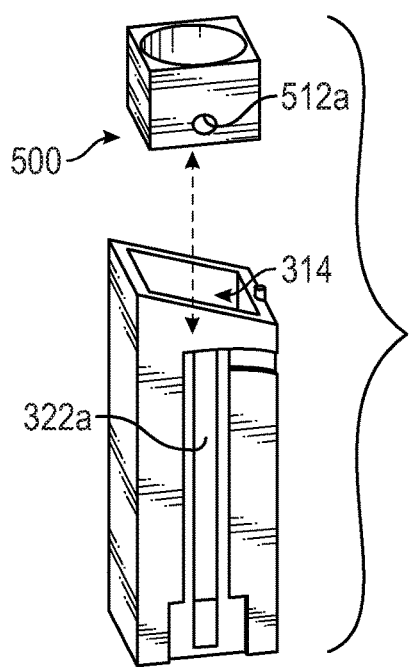
FIGS. 15A-15B show isometric views of the holder and the support cup of the applicator device having a square shaped support cup and a corresponding square shaped orifice and channel.
Figure 15B:
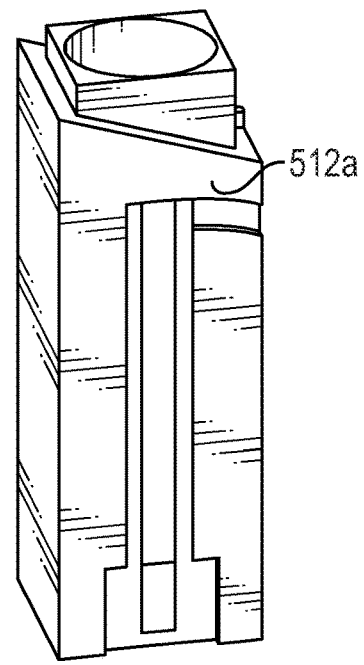
Figure 18:
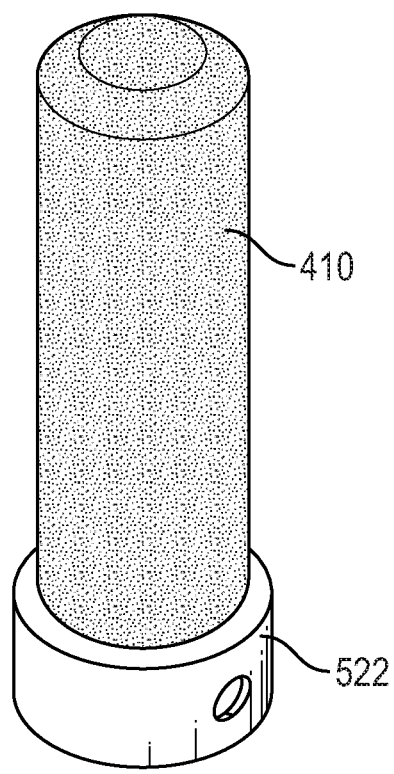
FIG. 18 shows an isometric view of a foam applicator assembled to the platform.

Alternatively, FIGS. 15A-15B show isometric views of the assembly of the holder 300 and the support cup 500 where a square shape is used for the support cup 500 and a corresponding square orifice and channel are provided on the holder 300. As shown in FIGS. 13A-13B, the non-circular profile makes it easier to orient the first recess 512a with the holder's first slot 322a. It is obvious from FIGS. 14A-15B that any non-circularly shaped support cup profile would allow easier orientation of the support cup recesses to the holder's slots during the assembly process.

Referring now to FIGS. 16A-18, various methods to hold the product 400 within the support cup 500 of the applicator device 100 are illustrated. Instead of inserting a solid product into a support cup, a wax or semi-solid product can be pierced with a stake 530 protruding from a top platform 522 as shown in FIGS. 16A-16B. The top platform 522 replaces the top opening 520 where the solid product was previously inserted and the side wall 510 continues to comprise the first recess 512a and the second recess 512b such that the outer shell's hinges can engage with the support cup.

Alternatively, the solid product can be wedged between a set of pillars 540 protruding from the platform 522 as shown in FIGS. 17A-17B. Even further, another method of containing the product within or on the support cup 500 would be to glue a foam applicator 410 or other reticulated material to the surface of the top platform 522 and embed the surface with liquid product. It is obvious that other vehicles for containing product may be incorporated into the applicator device 100, choice of which would depend on application and type of product.

Figure 19A:
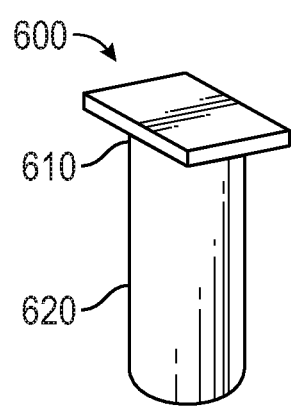
FIGS. 19A-19B are isometric views of the applicator device incorporating a seal.
Figure 19B:
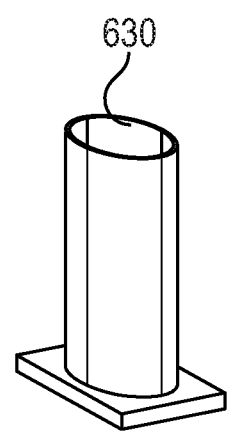

Referring now to FIGS. 19A-19B, isometric views of a seal 600 are illustrated. FIG. 19A is a top isometric view of the seal 600 showing a seal cover 610 and a seal tube 620. FIG. 19B is a bottom isometric view of the seal 600 showing a tube cavity 630 constructed within the seal tube 620.

Figures 20A, 20B:
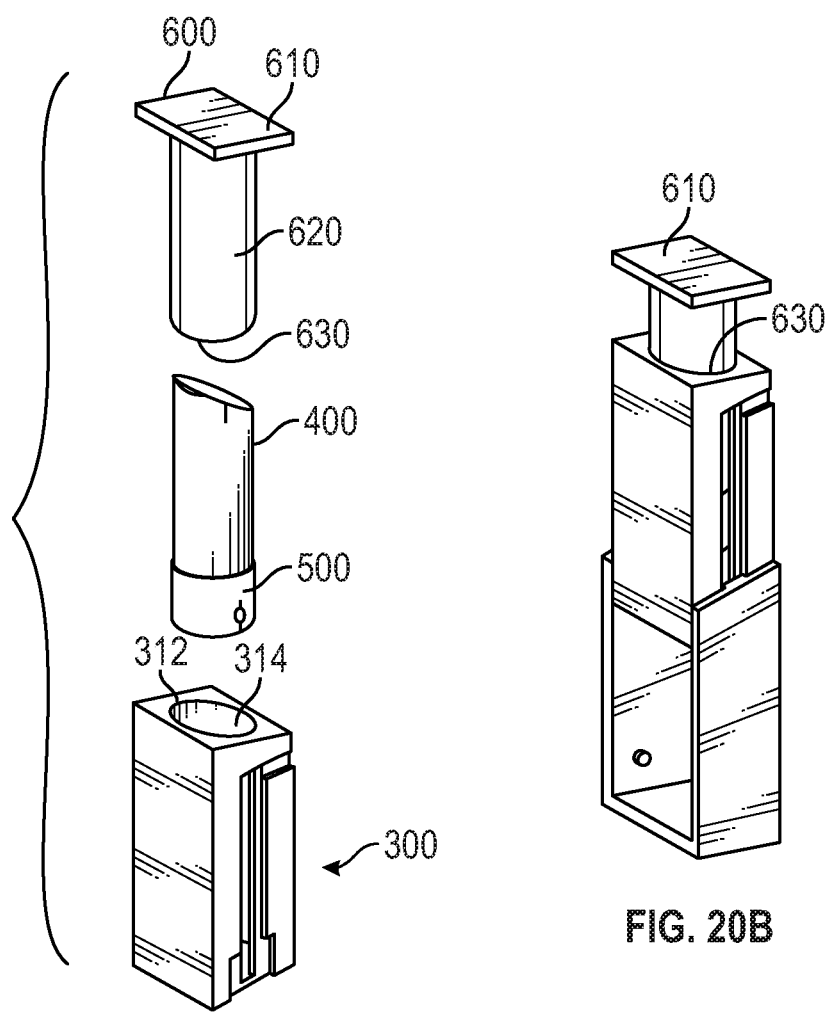
FIGS. 20A-20D are top isometric and cross-sectional views of the applicator device illustrating assembly of the seal along with the other components of the applicator device.

Referring now to the sealing feature of the applicator device, FIG. 20A shows an exploded view of relevant components of the applicator and their mutual relationships. The seal tube 620 is inserted around the exterior of the support cup 500 and through the orifice 312 and into the holder's channel 314. The product 400 simultaneously fits into the tube cavity 630. In FIG. 20A, the outer shell 200 is not shown.

FIG. 20B shows how the seal 600 is fitted over the holder 300 and the seal tube 620 fits through the orifice 312 forming an orifice-tube sealing feature. The orifice-tube seal is dimensioned such that there are no gaps through which air can travel. The outer shell 200 is shown in this figure, having rotated 180 degrees relative to the holder 300.

Figure 20C:
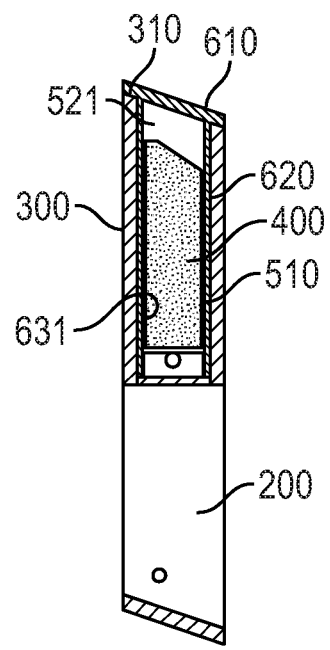

FIG. 20C is a cross-sectional view formed by a plane cutting midway between the first and second sides of the holder 300 and revealing the relationship between the critical components of a sealed applicator device. The outside hatched component is the holder 300. Inserted within the holder 300 is the seal tube 620 as described in FIG. 20B. The lower portion of the seal tube 620 is dimensioned such that the outer surface of the support cup's side wall 510 fills within the tube cavity 630 and a support cup-tube seal 631 is formed between the support cup 500 and the seal 600. The height of the tube cavity 630 is such that the product 400 can fit within its confines and the seal tube 620 can engage with the support cup's side wall 510 when the seal 600 is completely inserted within the channel 314 of the holder 300 and the seal cover 610 lays directly on top of the holder's top surface 310. Assuming the components contain no perforations other than those described hitherto, the product 400 is now completely sealed within the confines of the support cup 500 and the seal 600.

Figure 20D:
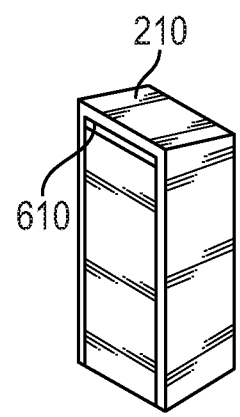

FIG. 20D is an isometric drawing of the closed and sealed applicator device with the outer shell cover 210 rotated over the seal cover 610. It should be noted that in this embodiment, the arms of the outer shell will be dimensioned slightly longer than in previously described embodiments in order to accommodate the added thickness of the seal cover 610 when the applicator device is completely closed.

Figure 21A:
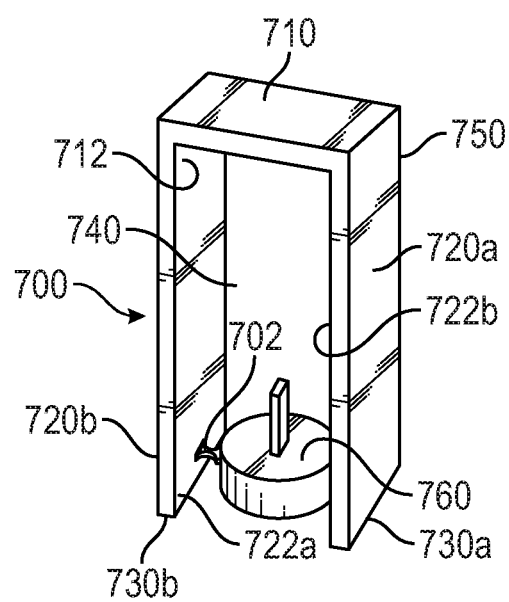

Referring now to another embodiment, FIG. 21A is an isometric view showing an outer shell 700 and a platform 760 of an exemplary two-piece applicator device. Similar to the outer shell 200 shown in FIG. 2A, this outer shell 700 consists of a cover 710 that is angled relative to its longitudinal axis. It has a first arm 720a and a second arm 720b, a first interior 722a and a second interior 722b, an underside 712 of the cover 710, a first base 730a and a second base 730b of the respective arms and a front opening 740 and a back opening 750. The first hinge 224a and second hinge 224b protrusions shown in FIG. 2A are replaced by living hinges 702 which connect to both sides of the platform 760.

Figure 21B:
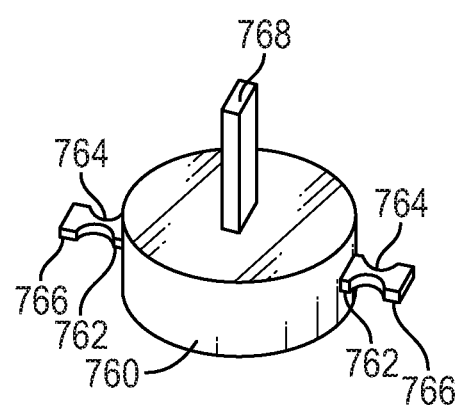

FIG. 21B shows a partial isometric magnified view of the platform 760. The platform 760 is connected to the outer shell's first and second interiors by virtue of a pair of living hinges 702. Each living hinge is comprised of three sections: a relatively flat platform connector 762 which is attached to the platform 760, an outer shell connector 766 which is attached to the outer shell arm's interiors and a bridge 764 which connects the platform connector 762 to the outer shell connector. The living hinges 702 are relatively flat compared to the height of the platform 760 and have an overall profile shape similar to an hourglass, with the narrow section of the hourglass being the bridge 764. The living hinges 702 can twist at the thinnest section being the bridge 764. On one flat side of the platform is a stake 768 that is designed to pierce and hold a product after filling.

FIG. 21C is an isometric top view of a holder 800 and FIG. 21D is an isometric bottom view of the same holder 800. Similar to the holder 300 as shown in FIG. 2B, there is a top surface 810, an orifice 812, a channel 814, a first slot 822a and a second slot 822b, a front side 830, a back side 840, and a first side 820a and a second side 820b. The bottom view clearly shows a bottom surface 850, a bottom opening 852 and two slits 854 positioned on opposite sides of the bottom opening 852. It will be shown in FIGS. 24-25 how the two slits extend into the first and second slots to allow assembly of the outer shell 700 to the holder 800.

FIGS. 22A-22B show cross-sectional front views of the exemplary two-piece applicator device illustrating how the product 400 is contained therein. The top sections of the drawings show the cross-sections of the holder 800. The drawings are cut longitudinally through the center of the first and second sides of the holder 800 revealing the first slot 822a and the second slot 822b, the orifice 812, the bottom opening 852, and the holder's channel 814. The bottom portions of the drawings show the cross-sections of the outer shell 700 fully rotated to an open position and the platform 760 and the stake 768 facing in an upward direction. The living hinges 702 extend through the first and second slots and connect to the outer shell 700.

Referring now to FIGS. 23A-23F, a sequence of isometric drawings of an exemplary two-piece applicator in various positions as it progresses from a completely closed position to an open position is illustrated. In each of the FIGS. 23A-23F is shown a corresponding isometric magnified detail of a platform portion of the applicator and its rotation relative to living hinges. For purpose of clarity, a holder is shown to be transparent so that the position of the platform and product can be clearly viewed.

Figure 23C:
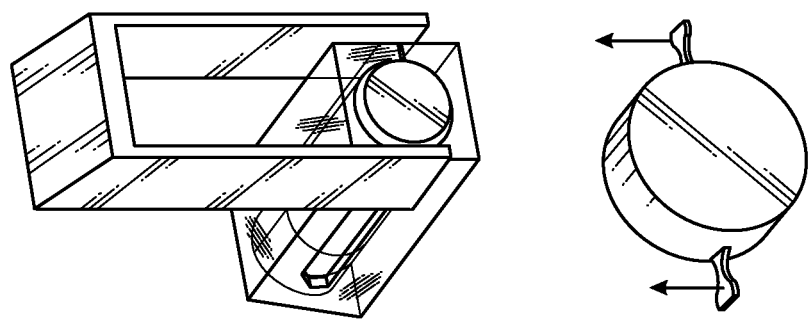
Figure 23B:
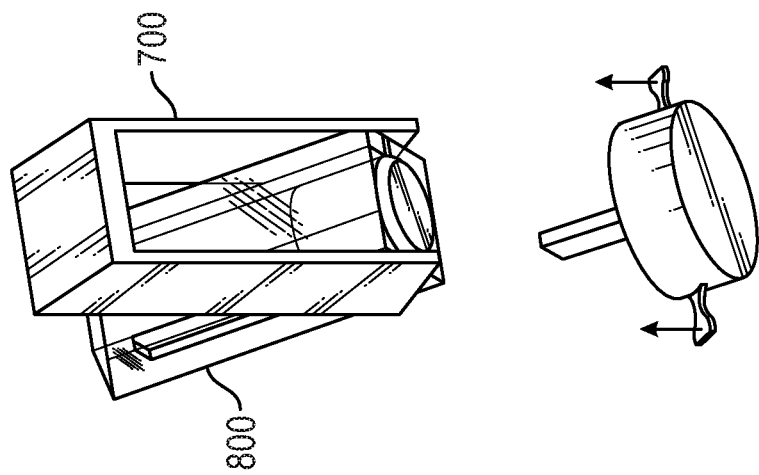
Figure 23A:
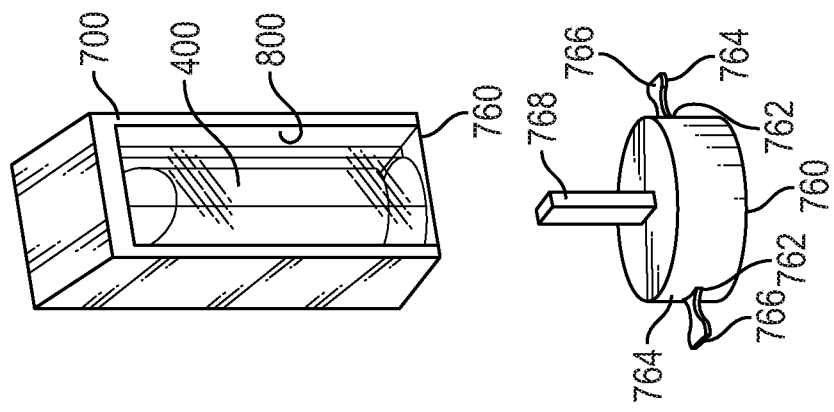

FIG. 23A shows the applicator device in a closed position. For example, the holder 800, the product 400 and the platform 760 are completely covered by the outer shell 700. The platform 760 of FIG. 23A is shown immediately below, including the platform connectors 762, the bridges 764 and the outer shell connectors 766 all facing in an upward direction. The stake 768 is shown to be perpendicular to the platform's upper surface.

FIG. 23B shows the applicator device as the holder 800 begins to rotate relative to the outer shell 700. The platform 760 and the stake 768 of FIG. 23B rotate about the bridges 764 of the living hinges 702 and relative to the outer shell connectors 766. The flat side of the outer shell connectors 766 remain facing in an upward direction as indicated by the pair of arrows, while the flat surfaces of the other components face in a different angular direction. The outer shell connectors 766 do not move relative to the outer shell 700.

FIGS. 23C-23E show the holder 800, the product 400 and the platform 760 continue to rotate relative to the outer shell 700 until the applicator device is in a completely open position. The lower magnified isometric drawings of FIGS. 23C-23E show the respective position of the platform 760, the platform connectors 762 and the stake 768 as they continue to rotate about the bridges 764 and relative to the outer shell connectors 766.

FIG. 23F shows the outer shell 700 push the platform 760 and propel the product 400 along the holder's channel 814 and through the holder's orifice 812. Because the design incorporates living hinges, the outer shell must be constructed out of a flexible material such as polypropylene.

Figure 24A:
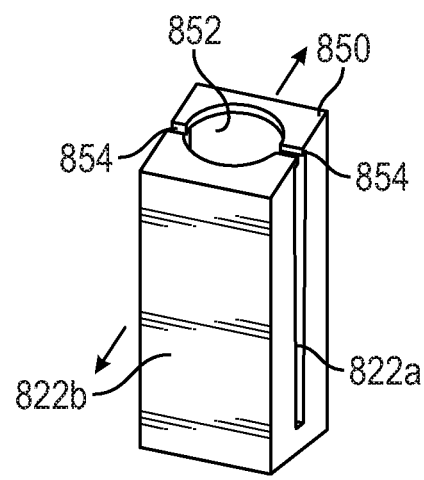
FIGS. 24A-24B are top and bottom isometric views respectively of the holder of the two-piece applicator device illustrating opening of the slits to allow insertion of the outer shell.
Figure 24B:
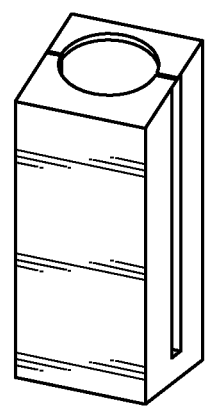

Referring now to FIGS. 24A-24B, top and bottom isometric views of the holder 800 of the two-piece applicator device illustrating how it can be opened to allow insertion and assembly of the outer shell 700, is shown.

FIG. 24A shows the bottom surface 850 of the holder 800 facing upwards to reveal the pair of slits 854 and the bottom opening 852. The holder 800 is pulled open in the directions of the opposing arrows so that the slits form an entrance for the outer shell 700 into the first slot 822a and the second slot 822b. FIG. 24B shows the same view with the pair of slits 854 reclosed. It is assumed that the slits 854 may be sealed together either mechanically using, for example, a tongue and groove pair, adhesive, or sonic or thermal sealing. As with the outer shell 700, the material of the holder 800 must be constructed out of a flexible material such as polypropylene.

Figure 25A:
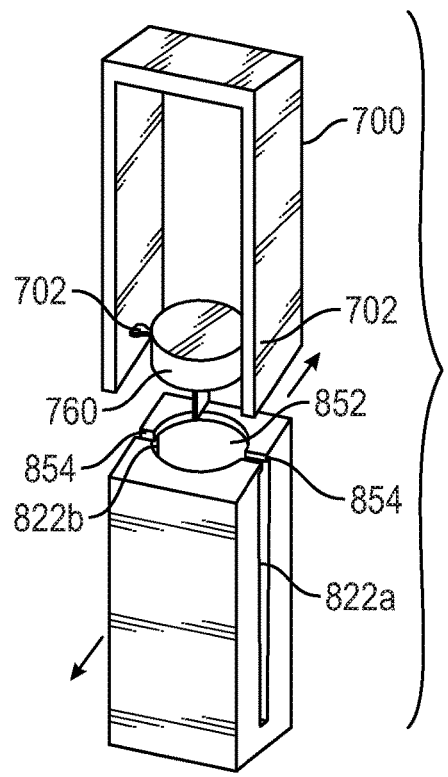
FIGS. 25A-25E show a sequence of isometric drawing of the two-piece applicator device as the outer shell is assembled to the holder.
Figure 25B:
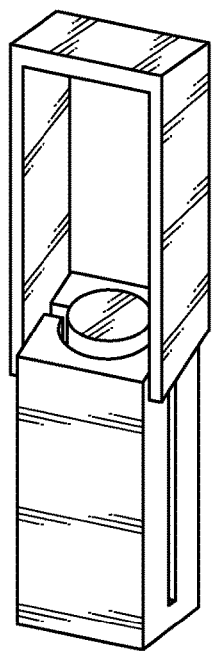
Figure 25C:
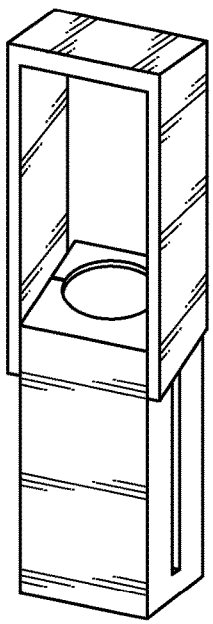
Figure 25D:
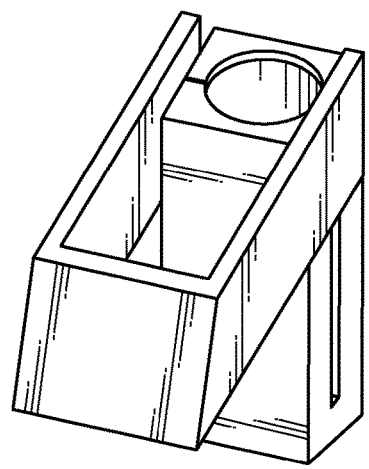
Figure 25E:
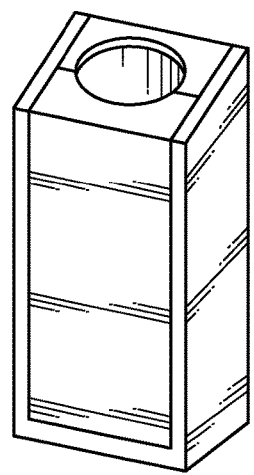

FIGS. 25A-25E show a sequence of isometric drawing segments of the two-piece applicator device as the outer shell 700 and the platform 760 are assembled to the holder 800. The holder 800 is shown with the bottom opening 850 facing upwards and the holder 800 is stretched open at in the direction of the arrows separating the holder 800 into two at the slits 854. The open slits lead into the respective slots and are open sufficiently wide to allow insertion of the living hinges 702 and the platform 760 as shown in FIG. 25B. FIG. 25C shows the holder's slits 854 now sealed together, the living hinges 702 completely inserted within the respective slots and the platform 760 within the channel 814. FIG. 25D shows the outer shell 700 rotating relative to the holder 800 toward a closed position. Finally, FIG. 25E shows the two-piece applicator device in a completely closed position.

FIGS. 26A-26G are various views that show an alternative way to prevent the holder from moving longitudinally relative to the shell when the device is closed. The holder contains an indentation or hole that locks with a corresponding peg located the outer shell when closed.

Figure 26A:
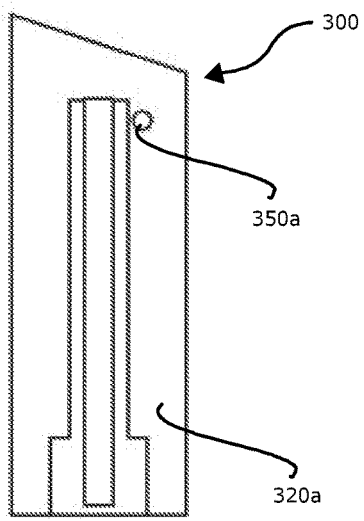
FIGS. 26A-26G are various views of embodiments that prevent a holder from moving longitudinally relative to a shell when the device is closed.

FIG. 26A shows the side view of the holder 300 with the holder's first side 320a containing a first indentation 350a.

Figure 26B:
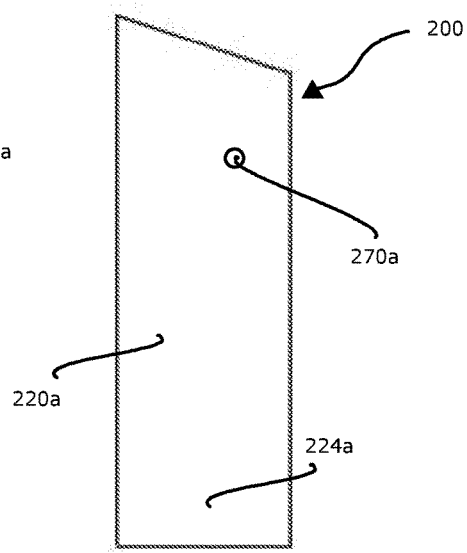

FIG. 26B shows the outer shell 200 containing a first peg 270a protruding from the outer shell's first arm 220a. There is a first hinge 224a located toward the bottom of the holder's first side 320a. The first peg 270a is configured such that it engages the first indentation 350a when the device is in a closed position. Though only the first side and the first arm of the device are described as containing these features, it is understood that the device can perform as described with or without corresponding indentation and peg incorporated on respectively the holder's second side and the outer shell's second arm.

Figure 26C:
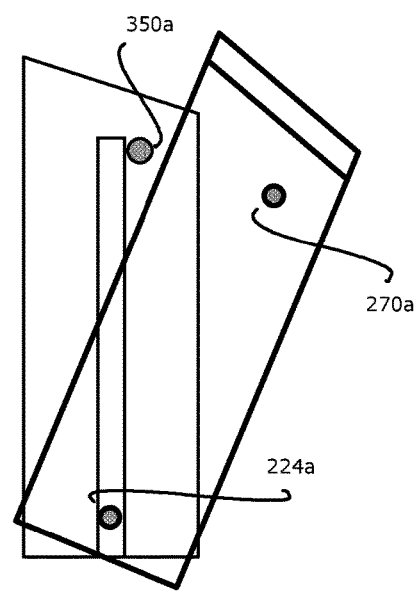

FIG. 26C shows the device where the outer shell is about to close against the holder as it rotates about the axis of the first hinge 224a. The first peg 270a is not yet proximal to the holder 300.

Figure 26D:
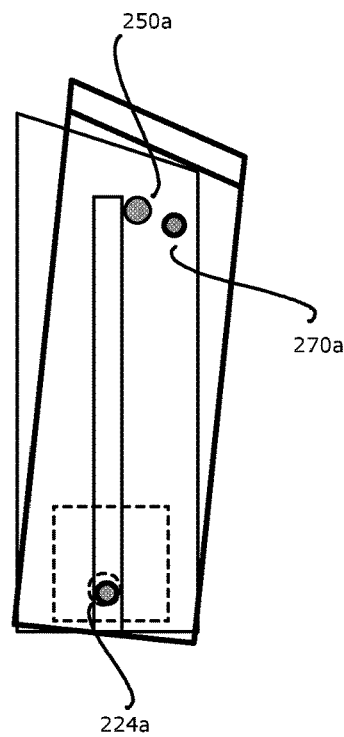

FIG. 26D shows the outer shell further rotating towards a closed position but the first peg 270a is now proximal to the holder as it continues to rotate about the first hinge 224a and migrates towards the first indentation 205a.

Figure 26E:
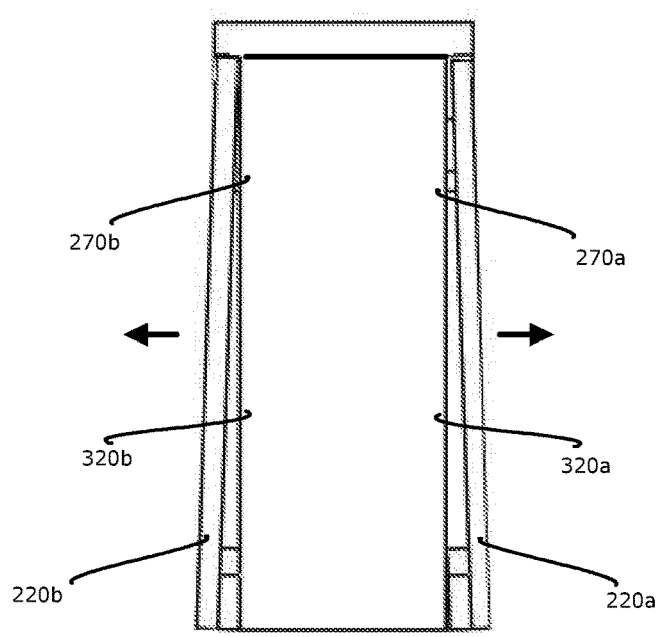

FIG. 26E shows the front view of the device. Also shown is the outer shell's first peg 270*a,* second peg 270*b* protruding respectively from a sufficiently bent first arm 220*a* and second arm. This occurs because as the pegs move proximal to the holder, they are temporarily pushed out respectively by the holder's first side 320*a* and second side 320*b,* in the directions of the shown arrows. Hence, the outer shell arms are constructed of a material suitably flexible to allow for this accommodation.

Figure 26F:
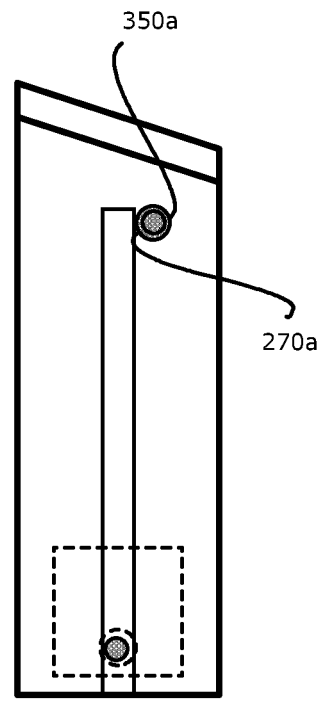

FIG. 26F shows a side view of the device in a closed position. The first peg 270*a* is engaged with the first indention 350*a.*

Figure 26G:
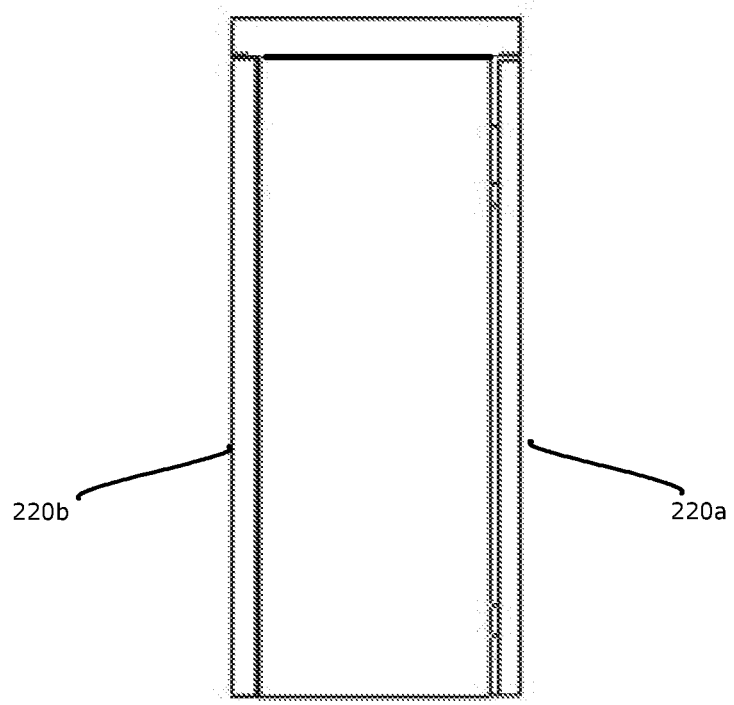

FIG. 26G shows a front view of the device with the outer shell's first arm 220*a* and second arm 220*b* in its unbent position.

FIGS. 27A-27F depict an embodiment wherein the lower position of the holder's guideway is configured such that it beneficially locks with the guide when the device is in a closed position.

Figure 27A:
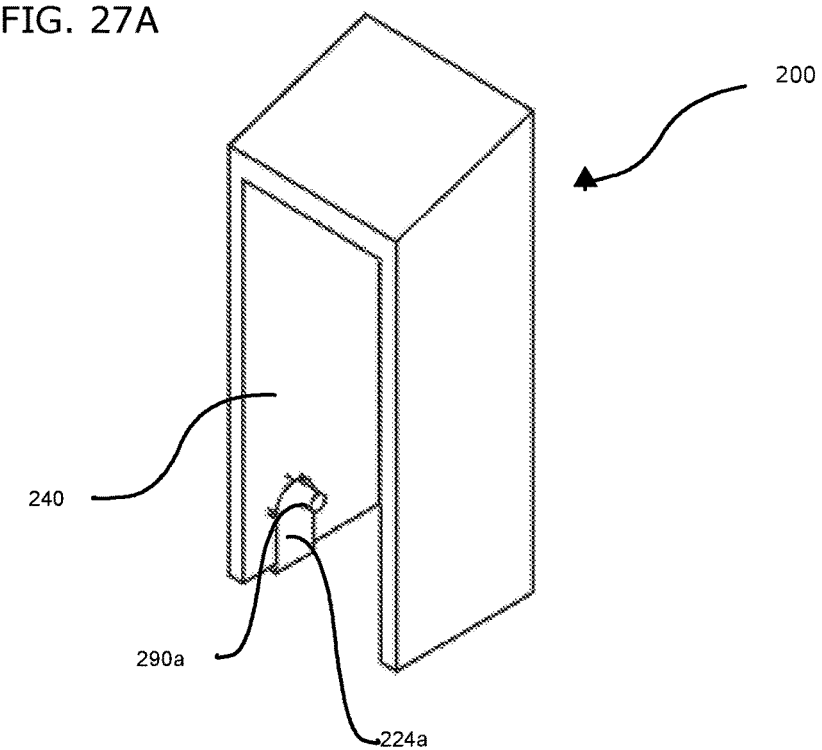
FIGS. 27A-27F depict another configuration that prevent a holder and outer shell from moving longitudinally relative to one another by virtue of configuring the lower position of the guideway such that it locks with the guide when the device is in a closed position.

FIG. 27A shows the back opening 240 view of the outer shell 200 from which protrudes a first guide 290*a* from which protrudes a first hinge 224*a.*

Figure 27B:
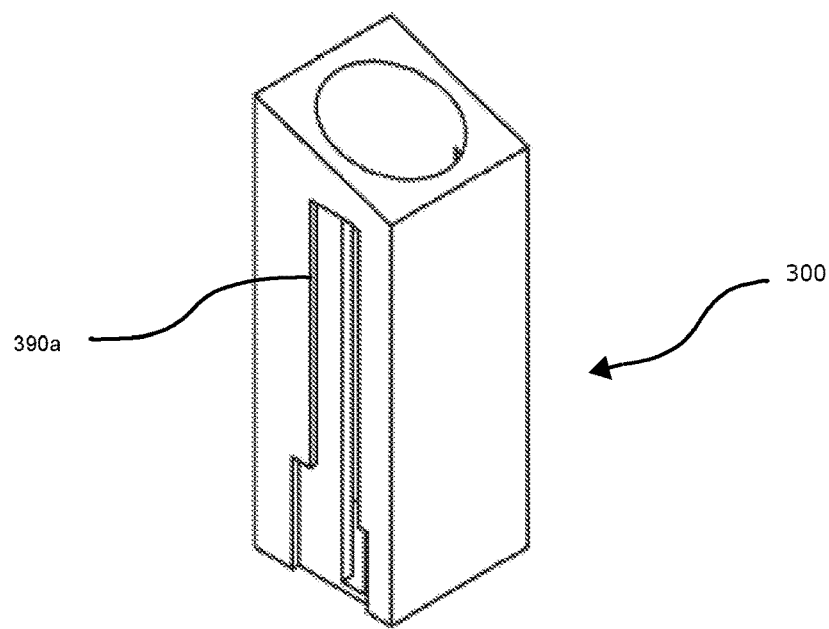
Figure 27C:
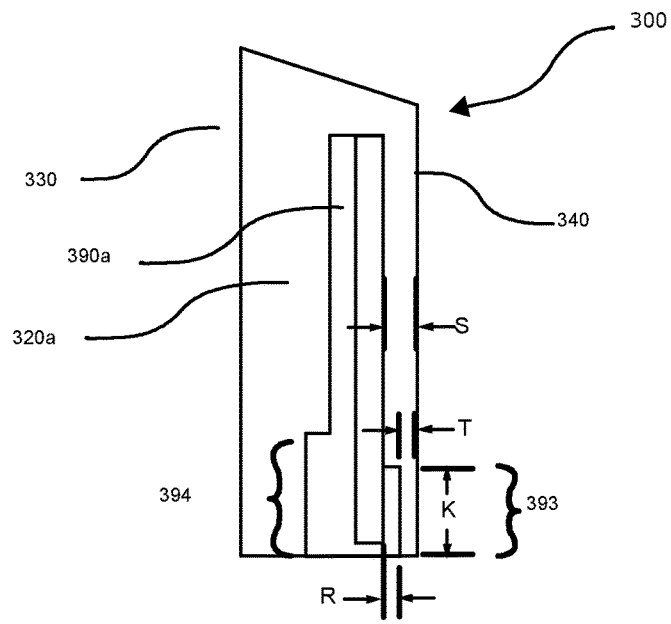

FIG. 27B shows a first guideway 390*a* inscribed in a holder 300. FIG. 27C shows a view of the holder's 300 first side 320*a* into which is inscribed a first guideway 390*a.* The lower portion 394 of the guideway 390*a* contains a lock section 393 of height K and length R, at an approximate distance T from the holder's back side 340.

Figure 27D:
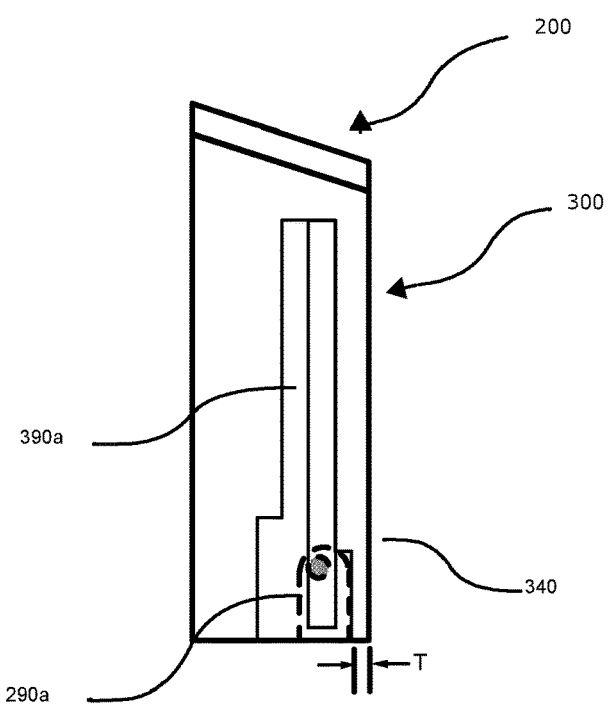

FIG. 27D shows a first side view of the device were the relevant components of the holder 300 are superimposed onto the outer shell 200 (bold outline) while the device is in a closed and locked position. The first guide 290*a* is engaged with the first guideway 390*a* such that the edges of both are positioned at an approximate distance T from the holder back side 340. In this position, a substantial portion of the first guide 290*a* is positioned within the lock section 393, such that the holder 300 is prevented from moving downwards, relative to the outer shell 200.

Figure 27E:
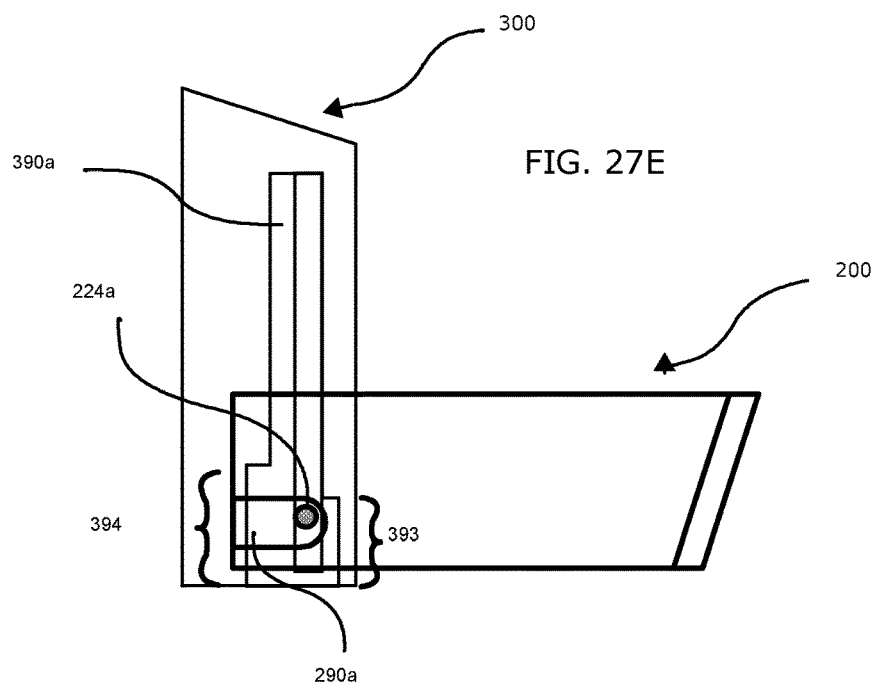

FIG. 27E shows the superimposed holder 300 and outer shell 200 where the outer shell has been rotated clockwise about the first hinge 224*a* away from the holder. The first guide 290*a* is now disengaged from the locked section 393 but still within the area of the lower portion 394 of the first guideway 390*a.*

Figure 27F:
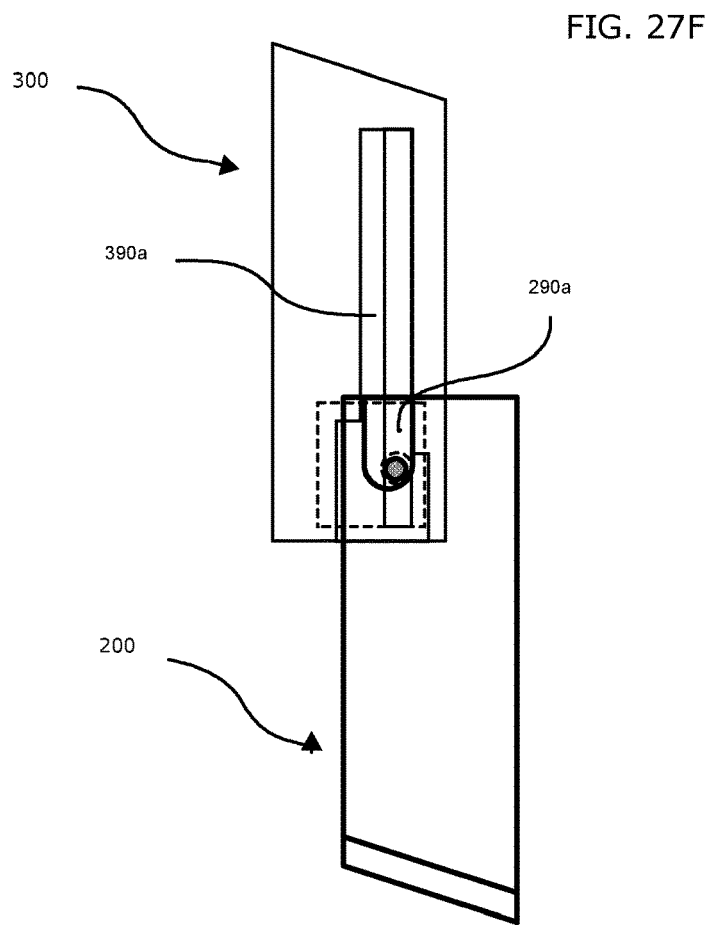

FIG. 27F shows the outer shell 200 sufficiently rotated from the holder 300, such that it can now move in a direction determined by the first guide 290*a* engagement along the first guideway 390*a.*

It should be understood that though the features described in FIGS. 27A-27F show exemplary interactions between a first guide and a first guideway, it is clear that the device can be designed with a corresponding second guide and second guideway on respectively the second arm of the outer shell and second side of the holder. Furthermore the drawing shows an outer shell with a slanted top allowing a clockwise rotational movement of the shell relative to the holder. Other configurations can be designed that are included within the scope of the invention described herein. For instance, the top of the outer shell and holder can be flat and the outer shell can rotate counter clockwise as well as clockwise.

Although illustrative embodiments have been described herein with reference to the accompanying drawings, it is to be understood that the invention is not limited to those precise embodiments, and that various other changes and modifications may be made by one skilled in the art without departing from the scope or spirit of the invention.

What is claimed is:

1. An applicator comprising:
a body having a first top surface including an opening, a channel extending through the body away from the opening of the first top surface, and a first side and a second side including a first slot and a second slot respectively cut through the first and second sides;
a cover having a second top surface, a first arm and a second arm extending away from the second top surface, and a first and second hinges installed on the first and second arms respectively;
a support cup having a side wall, an inner-body opening configured to receive a product, and first and second recesses inscribed on opposite sides of the side wall; and
an indentation or hole on at least one of the first and second sides of the body and a peg on at least one of the corresponding first and second arms of the cover such that when the indentation or hole engages with the peg, the cover is prevented from moving longitudinally with respect to the body,
wherein the support cup is slidably fitted inside the channel of the body and the cover is hingedly coupled to the body via the first and second hinges of the cover,
wherein the first and second hinges protrude through the first and second slots of the body and engage with the first and second recesses of the support cup, respectively, and the cover and the support cup are slidable together in a longitudinal direction along the channel of the body, and
wherein the body is configured to allow the cover and support cup to slide in the longitudinal direction only after the cover is rotated away from a position in which the opening is covered.

2. The applicator of claim 1, further comprising a male closure section either on the first top surface of the body or on an underside of the second top surface of the cover and a female closure section on the other of the first top surface or the underside of the second top surface.

3. The applicator of claim 1, wherein the support cup is not circular and the opening of the top surface and the channel of the body are correspondingly not circular.

4. The applicator of claim 1, wherein the first and second top surfaces are slanted with a predetermined angular offset.

5. The applicator of claim 1, wherein the applicator is in a closed position when the first top surface and the second top surface are aligned.

6. The applicator of claim 1, wherein the cover is transparent.

7. The applicator of claim 1, wherein the channel comprises a section configured to allow rotation of the cover, the section located distally from the opening.

8. An applicator comprising:
a body having a first top surface including an opening, a channel extending through the body away from the opening of the first top surface, and a first side and a second side including a first slot and a second slot respectively cut through the first and second sides;
a cover having a second top surface, a first arm and a second arm extending away from the second top surface, and a first and second hinges installed on the first and second arms respectively;
a support cup having a side wall, an inner-body opening configured to receive a product, and first and second recesses inscribed on opposite sides of the side wall; and a guideway inscribed into at least one of the first and second sides of the body and dimensionally configured such that when said guideway is engaged with the corresponding arms of the cover while in a closed position, the device cover is prevented from moving longitudinally with respect to the body, wherein the support cup is slidably fitted inside the channel of the body and the cover is hingedly coupled to the body via the first and second hinges of the cover, wherein the first and second hinges protrude through the first and second slots of the body and engage with the first and second recesses of the support cup, respectively, and the cover and the support cup are slidable together in a longitudinal direction along the channel of the body, and wherein the body is configured to allow the cover and support cup to slide in the longitudinal direction only after the cover is rotated away from a position in which the opening is covered.

9. The applicator of claim 8, wherein a guide in at least one of the first and second arms is offset from alignment with the corresponding guideway when the cover is in a closed position, preventing the cover from moving in the longitudinal direction.

10. The applicator of claim 9, wherein the guide is in alignment with the corresponding guideway when the cover is in an open position, allowing the cover to move in the longitudinal direction.

11. An applicator comprising:
a body having a first top surface including an opening, a channel extending through the body away from the opening of the first top surface, and a first side and a second side including a first slot and a second slot respectively cut through the first and second sides;

a cover having a second top surface, a first arm and a second arm extending away from the second top surface, and a first and second hinges installed on the first and second arms respectively;

a support cup having a side wall, an inner-body opening configured to receive a product, and first and second recesses inscribed on opposite sides of the side wall; and a guide embedded into at least one of the first and second sides of the body and dimensionally configured such that when said guide is engaged with a guideway embedded in the corresponding arm of the cover while in a closed position, the device cover is prevented from moving longitudinally with respect to the body, wherein the support cup is slidably fitted inside the channel of the body and the cover is hingedly coupled to the body via the first and second hinges of the cover, wherein the first and second hinges protrude through the first and second slots of the body and engage with the first and second recesses of the support cup, respectively, and the cover and the support cup are slidable together in a longitudinal direction along the channel of the body, and wherein the body is configured to allow the cover and support cup to slide in the longitudinal direction only after the cover is rotated away from a position in which the opening is covered.

12. The applicator of claim 11, wherein the guide is in alignment with the corresponding guideway when the cover is in an open position, allowing the cover to move in the longitudinal direction.

\* \* \* \* \*